(12) United States Patent
Bamdad

(10) Patent No.: US 9,932,407 B2
(45) Date of Patent: Apr. 3, 2018

(54) STEM CELL ENHANCING THERAPEUTICS

(71) Applicant: Minerva Biotechnologies Corporation, Waltham, MA (US)

(72) Inventor: Cynthia Bamdad, Waltham, MA (US)

(73) Assignee: Minerva Biotechnologies Corporation, Waltham, MA (US)

( * ) Notice: Subject to any disclaimer, the term of this patent is extended or adjusted under 35 U.S.C. 154(b) by 12 days.

(21) Appl. No.: 14/622,677

(22) Filed: Feb. 13, 2015

(65) Prior Publication Data

US 2015/0299334 A1    Oct. 22, 2015

Related U.S. Application Data

(63) Continuation of application No. PCT/US2013/055015, filed on Aug. 14, 2013, which is a continuation-in-part of application No. PCT/US2012/060684, filed on Oct. 17, 2012, and a continuation-in-part of application No. PCT/US2013/025981, filed on Feb. 13, 2013.

(60) Provisional application No. 61/683,155, filed on Aug. 14, 2012, provisional application No. 61/684,654, filed on Aug. 17, 2012, provisional application No. 61/693,712, filed on Aug. 27, 2012, provisional application No. 61/837,560, filed on Jun. 20, 2013.

(51) Int. Cl.
*C07K 16/30* (2006.01)
*C07K 16/28* (2006.01)

(52) U.S. Cl.
CPC .......... *C07K 16/3092* (2013.01); *C07K 16/28* (2013.01); *C07K 2317/30* (2013.01); *C07K 2317/33* (2013.01); *C07K 2317/34* (2013.01); *C07K 2317/35* (2013.01); *C07K 2317/73* (2013.01); *C07K 2317/74* (2013.01)

(58) Field of Classification Search
None
See application file for complete search history.

(56) References Cited

U.S. PATENT DOCUMENTS

| | | | |
|---|---|---|---|
| 5,342,947 A | * | 8/1994 | Lackey ............... C07D 491/22 540/470 |
| 7,825,092 B2 | | 11/2010 | Vesely |
| 2009/0075926 A1 | | 3/2009 | Bamdad |
| 2010/0316688 A1 | | 12/2010 | Bamdad |

FOREIGN PATENT DOCUMENTS

| | | | | |
|---|---|---|---|---|
| CN | 101652469 | | 2/2010 | |
| CN | 102549146 | | 7/2012 | |
| EP | 2329822 | | 8/2001 | |
| WO | 199109134 A1 | | 6/1991 | |
| WO | 2006105448 A2 | | 5/2006 | |
| WO | 2008101231 | | 2/2008 | |
| WO | 2008/070171 A2 | | 6/2008 | |
| WO | 2010/042891 A2 | | 4/2010 | |
| WO | WO2010/042562 | * | 4/2010 | ........... A61K 39/395 |
| WO | 2003/020279 A2 | | 3/2013 | |

OTHER PUBLICATIONS

Wheeler (Salud p'ublica de M'exico, 1997, vol. 39, pp. 283-287).*
Efferson et al (Anticancer research, 2005, vol. 25, pp. 715-724).*
Bachman et al (Journal of Immunology, 2005, vol. 175, pp. 4677-4685).*
Katayose et al (Cancer Research, 1996, vol. 56, pp. 4205-4212).*
Aboud-Pirak et al (PNAS, 1989, vol. 86, pp. 3778-3781).*
Mahanta et al, PLoS One, 2008, vol. 3, e2054, 12 pages.*
Lyman (Current Opinion in Hematology, 2010, vol. 18, pp. 1-10).*
Hikita, Sherry et al., "MUC1 Mediates the Growth of Human Pluripotent Stem Cells," PLoS ONE 3(10):1-13.
Brugger et al., "Expression of MUC-1 Epitopes on Normal Bone Marrow: Implications for the Detection of Micrometastatic Tumor Cells," Journal of Clinical Oncology, vol. 17, No. 5, 1999: pp. 1535-1544.
Ikezoe et al., "A novel treatment strategy targeting Aurora kinases in acute myelogenous leukemia," Molecular Cancer Therapy vol. 6, 2007 pp. 1851-1857.
International Search Report from counterpart PCT application PCT/US13/55015, dated Mar. 7, 2014.
Igakuno Ayumi, 2006,vol. 217, No. 5, pp. 434-438.

* cited by examiner

*Primary Examiner* — Karen A. Canella
(74) *Attorney, Agent, or Firm* — Joseph Hyosuk Kim; JHK Law

(57) ABSTRACT

The present application disclose a method for treating a patient who would benefit from stimulation of the patient's stem cells, comprising administering to the patient an antibody that specifically binds to an epitope of the MUC1 protein expressed on human undifferentiated stem cells.

38 Claims, 33 Drawing Sheets

The Fab of cancer cell antibody C2-FAB has no effect on growth of BGO1V stem cell growth
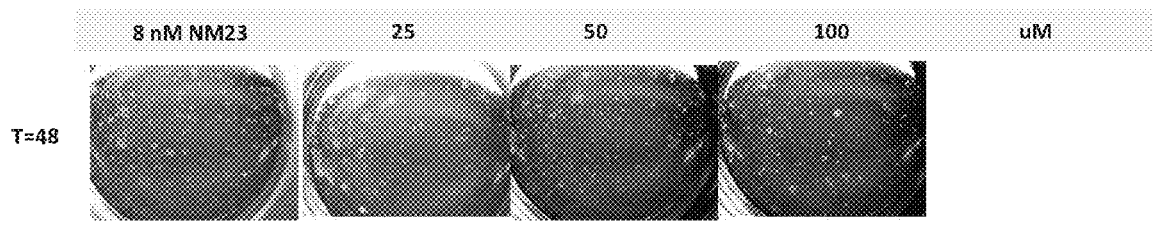
The Fab of stem cell antibody C3-FAB inhibits stem cell growth as a function of Fab concentration
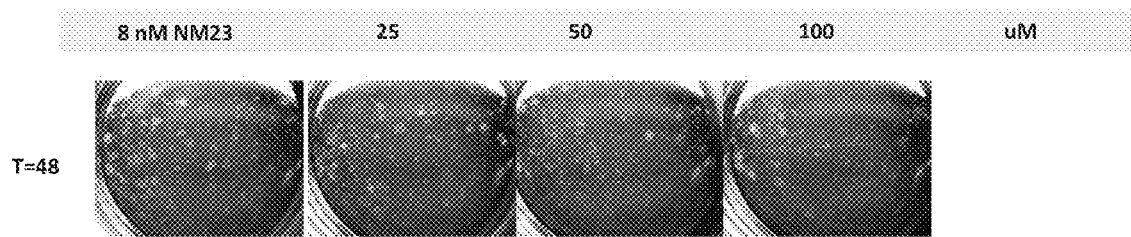
Fig. 10

The Fab of cancer cell antibody C2-FAB has no effect on growth of BGO1V stem cell growth

| 8 nM NM23 | 12.5 | 25 | 50 | 100 | µM |

T=96

8 nM NM23　　12.5　　25　　50　　100　　µM

The Fab of cancer cell antibody E6-FAB has no effect on growth of BGO1V stem cell growth

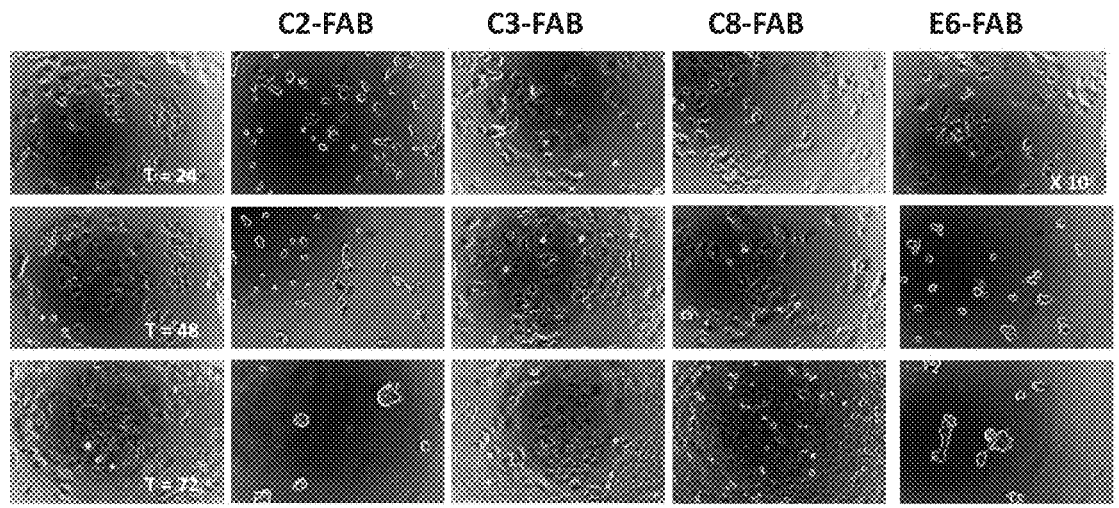
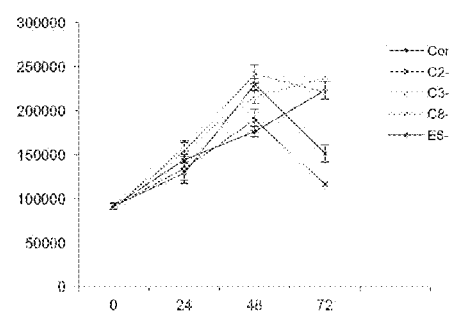
Fig. 14

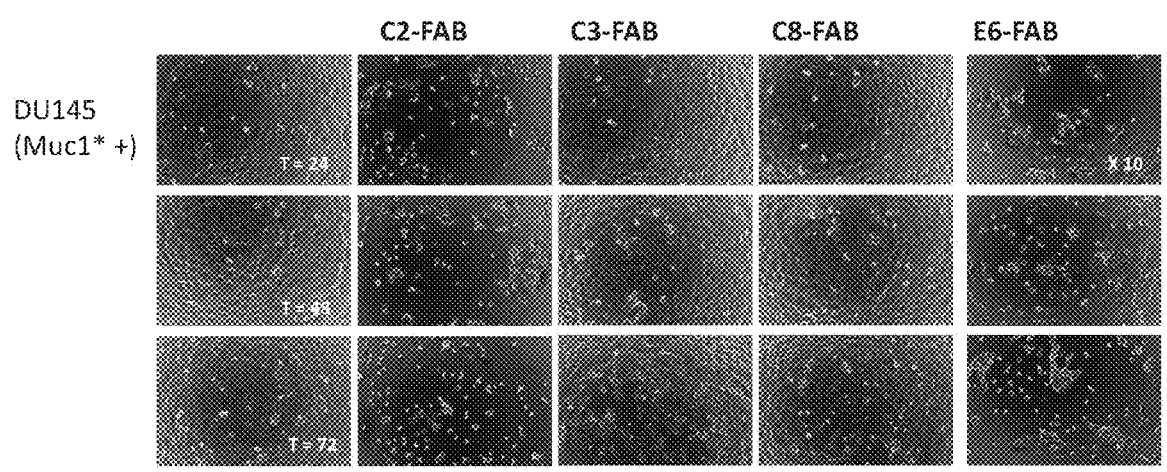
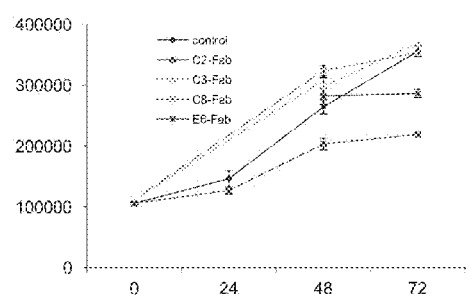
Fig. 15

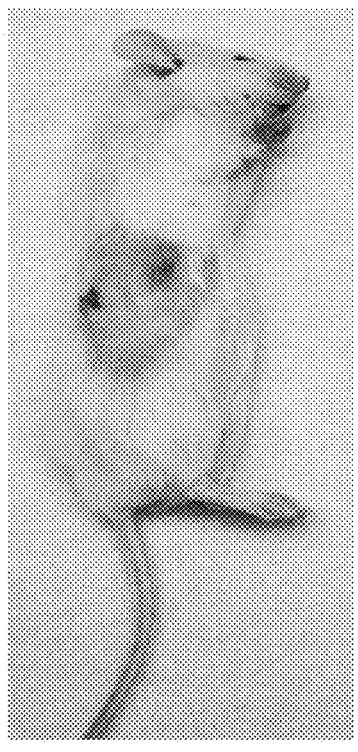
Mouse 2  Mouse 5  Mouse 12
Group 2 Mice
Untreated (Vehicle)
Fig. 22

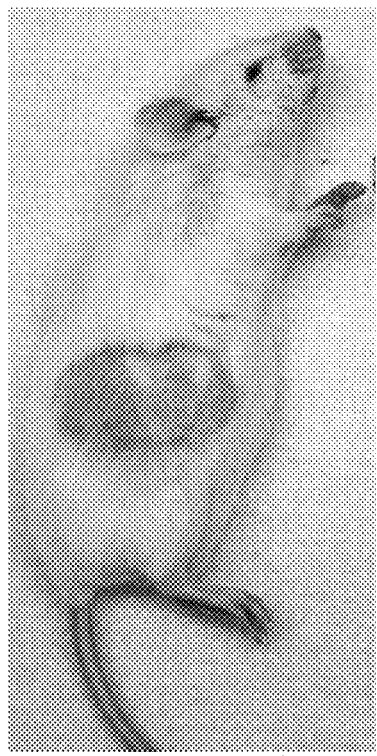 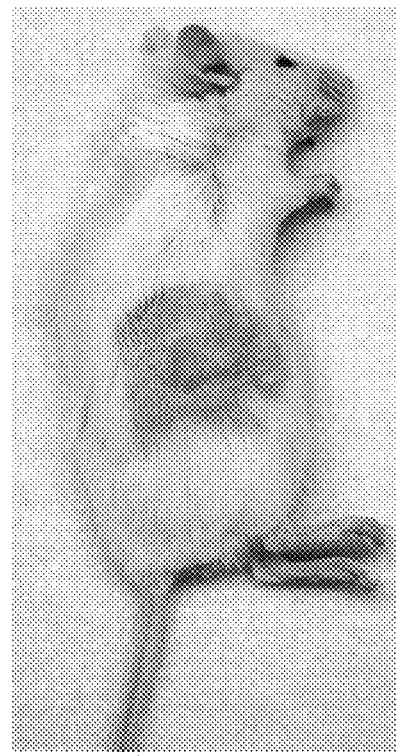
Mouse 4     Mouse 22
Group 3 Mice
FAB Treated
Fig. 23

Anti MUC1* IgG monoclonal antibody light chain variable region sequences

| | FWR1 | CDR1 | FWR2 | CDR2 |
|---|---|---|---|---|
| MIN-C2 | DIVITQSTASLGVSLGQRATISC | RASKSVSTSGYSYMH | WYQQRPGQPPKLLIY | LASNLES |
| MIN-E6 | DIVITQTTAIMSASPGEEVTLTC | SATSSV------SYIH | WFQQRPGTSPKLWIY | STSNLAS |
| MIN-A2-1 | DIVLTQSTEIMSASPGEKVTITC | SASSSI------SYIH | WFQQKPGTSPKLWIF | GTSNLAS |
| MIN-A2-2 | DIVMTQSPAIMSASPGEKVTMTC | SASSSV------SYIH | WFQQKPGTSPKLWIY | STSNLAS |
| MIN-C9-1 | DIVLTQTTAIMSASPGEKVTITC | SASSSV------SYMY | WFQQKPGTSPKLWIY | STSNLAS |
| MIN-C9-2 | DIVITQSTAIMSASPGEKVTMTC | SASSSV------SYTY | WFQQKPGTSPKLWIY | STSNLAS |
| MIN-D7-1 | DIVITQTPAIMSASPGEKVTMTC | SASSSV------SYMH | WFQQKPGTSPKLWIY | STSNLAS |
| MIN-D7-2 | DIVLTQSTAIMSASPGEKVTMTC | SASSSV------SYMH | WFQQKPGTSPKLWIY | STSNLAS |
| MIN-F2-1 | DIVMTQSPEIMSASPGEKVTITC | SASSSI------SYIH | WFQQKPGTSPKLWIF | GTSNLAS |
| MIN-F2-2 | DIVITQSTEIMSASPGEKVTITC | SASSSI------SYIH | WFQQKPGTSPKLWIF | GTSNLAS |

| | FWR3 | CDR3 | |
|---|---|---|---|
| MIN-C2 | GVPARFSGSGSGTDFTLNIHPVEEEDAATYYC | QHSRELPFT | FGGGTKLEIKRADAAPTVS |
| MIN-E6 | GVPVRFSGSGSGYGTSYSLTISRMEAEDAATYYC | QQRSSSPFT | FGSGTKLEIKRADAAPTVS |
| MIN-A2-1 | GVPARFSGSGSGTSYSLTVSRMEAEDAATYYC | QQRSNYPFT | FGSGTKLQIKRADAAPTVS |
| MIN-A2-2 | GAPARFSGSGSGTSYSLTVSRMESEDAATYYC | QQRSSYPST | FGGGTKLEIKRADAAPTVS |
| MIN-C9-1 | GVPARFSGSGSGTSYSLTIISRMEAEDAATYYC | QQRSSYPST | FGGGTKLEIKRADAAPTVS |
| MIN-C9-2 | GVPARFSGSGSGTSYSLTISRMEAEDAATYYC | QQRSSYPST | FGGGTKLEIKRADAAPTVS |
| MIN-D7-1 | GVPARFSGSGSGTSYSLTVSRMESEDAATYYC | QQRSSYPST | FGGGTKLEIKRADAAPTVS |
| MIN-D7-2 | GVPARFSGSGSGTSYSLTVSRMESEDAATYYC | QQRSSYPST | FGGGTKLEIKRADAAPTVS |
| MIN-F2-1 | GVPARFSGSGSGTSYSLTVSRMEAEDTATYYC | QQRSNYPFT | FGSGTKLQIKRADAAPTVS |
| MIN-F2-2 | GVPARFSGSGSGTSYSLTVSRMEAEDTATYYC | QQRSNYPFT | FGSGTKLQIKRADAAPTVS |

Fig. 24

Anti MUC1* IgG monoclonal antibody heavy chain variable region sequences

| | FWR1 | CDR1 | FWR2 | CDR2 |
|---|---|---|---|---|
| MIN-C2 | EVQLEESGGGLVKPGGSLKLSCAASGFTFS | GYAMS | WVRQTPEKRLEWVA | TISSGGTYIYY |
| MIN-E6-7 | EVKLEESGGDLVKPGGSLKLSCAASGFTFS | RYGMS | WVRQTPDKRLEWVA | TISSGGTYIYY |
| MIN-E6-8 | EVKLEESGGDLVKPGGSLKLSCVVSGFTFS | RYGMS | WVRQTPGKRLEWVA | TISSGGGTYIYY |
| MIN-A2-1 | EVKLQESGPELKKPGETVEISCKASGYTFT | NYGMN | WVKQAPGKGLKWMG | WINTYTGEPTY |
| MIN-A2-2 | EVQLQQSGPELKKPGETVKISCKASGYTFT | NYGMN | WVKQAPGKGLKWMG | WINTYTGEPTY |
| MIN-C9-1 | QVQLQESGPELKQPGETVKISCKASGYTFT | NNGMN | WVKQAPGKGLKWMG | WINTYTGEPTY |
| MIN-C9-2 | QVQLQQSGPELKQPGETVKISCKASGYTFT | NNGMN | WVKQAPGKGLKWMG | WINTYTGEPTY |
| MIN-D7-1 | EVQLEQSGPELKKPGETVKISCKASGYTFI | NYGMN | WVKQAPGKGLKWMG | MINTYTGEPTY |
| MIN-D7-2 | EVQLQQSGPELKKPGETVKISCKASGYTFI | NYGMN | WVKQAPGKGLKWMG | WINTYTGEPTY |
| MIN-F2-1 | EVKLEESGPELKKPGETVKISCKASGYTFI | NYGMN | WVKQAPGKGLKWMG | WINTYTGEPTY |
| MIN-F2-2 | EVQLQSGAELVRPGASVKLSCKALGYTFT | DYEMH | WVKQTPVHGLEWIG | AIHPGSGGTAY |
| MIN-F2-2 | RCRLQQSGPELKKPGETVKISCKASGYTFI | NYGMN | WVKQAPGKGLKWMG | WINTYTGEPTY |
| MIN-F2-3 | | | | |
| MIN-F2-4 | EVQLEQSGPELKKPGETVKISCKASGYTFI | NYGMN | WVKQAPGKGLKWMG | WINTYTGEPTY |

| | FWR3 | CDR3 | |
|---|---|---|---|
| MIN-C2 | RFTISRDNAKNTLYLQMSSLRSEDTAMYYCAR | LGGDNYY-EY | FDVWGAGTTVTVSSAKTTPPSVY |
| MIN-E6-7 | RFTISRDNAKNTLYLQMSSLKSEDTAMYYCAR | DNYGSSYDYA | MDYWGQGTSVTVSSAKTTAPSVY |
| MIN-E6-8 | RFTISRDNAKNTLYLQMSSLKSEDTAMYHCTR | DNYGRNYDYG | MDYWGQGTSVTVSSAKTTAPSVY |
| MIN-A2-1 | RFAFSLETSASTAYLQINTLKNEDTATYFCAR | SGDGYWY-YA | MDYWGQGTSVTVSSAKTTPPSVY |
| MIN-A2-2 | RFAFSLETSASTAYLQINTLKNEDTATYFCAR | SGDGYWY-YA | MDYWGQGTSVTVSSAKTTPPSVY |
| MIN-C9-1 | RFAFSLDTSASTAYLQINNLKNEDMATYFCAR | TGTARAF-YA | MDYWGQGTSVTVSSTKTTAPSVY |
| MIN-C9-2 | RFAFSLGTSASTAYLQINNLKNEDMATYFCAR | TGTARAF-YA | MDYWGQGTSVTVSSIKTTAPSVY |
| MIN-D7-1 | RFAFSLETSARTAYLQINNLKNEDMATYFCAR | TGTTAIL-NG | MDYWGQGTSVTVSSAKTTPPSVY |
| MIN-D7-2 | RFAFSLETSARTAYLQINNLKNEDTATYFCAR | SGDGYWY-YA | MDYWGQGTSVTVSSAKTTPPSVY |
| MIN-F2-1 | RFAFSLETSARTAYLQINNLKNEDMATYFCAR | TGTTAIL-NG | MDYWGQGTSVTVSSAKTTPPSVY |
| MIN-F2-2 | KATLTADKSSSTAYMELSSLTSEDSAVYYCTN | YGSFA----- | --YNGQGTLVTVSSAAKTTPPSVY |
| MIN-F2-3 | RFAFSLETSARTAYLQINNLKNEDMATYFCAR | TGTTAIL-NG | MDYWGQGTSVTVSSAKTTPPSCL |
| MIN-F2-4 | RFAFSLETSARTAYLQINNLKNEDMATYFCAR | TGTTAIL-NG | MDYWGQGTSVTVSSAKTTPPSVY |

Fig. 25

2D6C3 Kappa Chain Variable Region

```
←———— FWR1 ————→ ←———— CDR1 ————→
DIVITQTPLSLPVSLGDQASISCRSSQTIVHSNGNTYLE
←———— FWR2 ————→ ←— CDR2 —→ ←
WYLQKPGQSPKLLIYKVSNRFSGVPDRFSGSGSG
←———— FWR3 ————→ ←— CDR3 —→
TDFTLKINRVEAEDLGVYYCFQGSHVPFT
```

Fig. 28

2D6C3 Heavy Chain Variable Region

```
     ←─────────── FWR1 ───────────→←─CDR1─→←─
     EVMVVESGGGLVKPGGSLKLSCAASGFTFSGYAMSWVRQTPE
     ── FWR2 ──→←───── CDR2 ─────→←─────────────
     KRLEWVATISSGGTYIYYPDSVKGRFTISRDNAKNTLYLQMSSL
     ─── FWR3 ───────→←── CDR3 ───→
     RSEDTAMYYCARLGGDNYYEY
```

Fig. 29

2D6C8 Kappa Chain Variable Region

```
         ◄─────── FWR1 ────────► ◄────── CDR1 ──────► ◄──
         DIVITQTPASLAVSLGQRATISYRASKSVSTSGYSYMHWN
         ─── FWR2 ────► ◄─ CDR2 ─► ◄────────── FWR3 ──────
         QQKPGQPPRLLIYLVSNLESGVPARFSGSGSGTDFTLNIH
         ──────────►◄─── CDR4 ────►
         PVEEEDAATYYCQHIRELTRSE
```

Fig. 30

2D6C8 Heavy Chain Variable Region

```
←————————— FWR1 —————————→ ←CDR1→ ←—————
EVMVVESGGGLVKPGGSLKLSCAASGFTFSGYAMSWVRQTPE
 FWR2 ————→ ←————— CDR2 —————→ ←—————————
KRLEWVATISSGGTYIYYPDSVKGRFTISRDNAKNTLYLQMSSL
 FWR3 —————————→ ←——— CDR3 ———→
RSEDTAMYYCARLGGDNYYEY
```

Fig. 31

3C2B1 Kappa Chain Variable Region

<----------- FWR1 -----------> <----------- CDR1 -----------> <--
DIVLTQSPASLAVSLGQRATISCRASKSISTSDYNYIHWYQQK
---- FWR2 ----> <-- CDR2 --> <----------- FWR3 -----------
PGQPPKLLIYLASNLESGVPARFSGSGSGTDFTLNIHPVEEED
----> <---- CDR3 ---->
AATYYCQHSRELPLTF

Fig. 32

3C2B1 Heavy Chain Variable Region

```
←———————— FWR1 ————————→ ←— CDR1 —→ ←—
EVMLVESGGGLVKPGGSLKLSCAASGITFSTYTMSWVR
——— FWR2 ———→ ←——— CDR2 ———→ ←————
QTPEKRLEWVATISTGGDKTYYSDSVKGRFTISRDNAK
——————— FWR3 ———————→ ←——— CDR3 ———→
NNLYLQMSSLRSEDTALYYCARGTTAMYYYAM
```

Fig. 33

```
                        SEQUENCE LISTING

<160> NUMBER OF SEQ ID NOS: 87

<210> SEQ ID NO 1
<211> LENGTH: 45
<212> TYPE: PRT
<213> ORGANISM: Artificial Sequence
<220> FEATURE:
<223> OTHER INFORMATION: PSMGFR

<400> SEQUENCE: 1

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 2
<211> LENGTH: 26
<212> TYPE: PRT
<213> ORGANISM: Artificial Sequence
<220> FEATURE:
<223> OTHER INFORMATION: PSMGFR related sequence

<400> SEQUENCE: 2

Gly Phe Leu Gly Leu Ser Asn Ile Lys Phe Arg Pro Gly Ser Val Val
1               5                   10                  15

Val Gln Leu Thr Leu Ala Phe Arg Glu Gly
            20                  25

<210> SEQ ID NO 3
<211> LENGTH: 35
<212> TYPE: PRT
<213> ORGANISM: Artificial Sequence
<220> FEATURE:
<223> OTHER INFORMATION: PSMGFR related sequence

<400> SEQUENCE: 3

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35

<210> SEQ ID NO 4
<211> LENGTH: 35
<212> TYPE: PRT
<213> ORGANISM: Artificial Sequence
<220> FEATURE:
<223> OTHER INFORMATION: PSMGFR related sequence
```

<400> SEQUENCE: 4

```
Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val
        35
```

<210> SEQ ID NO 5
<211> LENGTH: 10
<212> TYPE: PRT
<213> ORGANISM: Artificial Sequence
<220> FEATURE:
<223> OTHER INFORMATION: PSMGFR related sequence

<400> SEQUENCE: 5

```
Val Val Gln Leu Thr Leu Ala Phe Arg Glu
1               5                   10
```

<210> SEQ ID NO 6
<211> LENGTH: 45
<212> TYPE: PRT
<213> ORGANISM: Artificial Sequence
<220> FEATURE:
<223> OTHER INFORMATION: PSMGFR related sequence

<400> SEQUENCE: 6

```
Val Val Gln Leu Thr Leu Ala Phe Arg Glu Gly Thr Ile Asn Val His
1               5                   10                  15

Asp Val Glu Thr Gln Phe Asn Gln Tyr Lys Thr Glu Ala Ala Ser Arg
            20                  25                  30

Tyr Asn Leu Thr Ile Ser Asp Val Ser Val Ser Asp Val
            35                  40                  45
```

<210> SEQ ID NO 7
<211> LENGTH: 26
<212> TYPE: PRT
<213> ORGANISM: Artificial Sequence
<220> FEATURE:
<223> OTHER INFORMATION: PSMGFR related sequence

<400> SEQUENCE: 7

```
Ala Ser Arg Tyr Asn Leu Thr Ile Ser Asp Val Ser Val Ser Asp Val
1               5                   10                  15

Pro Phe Pro Phe Ser Ala Gln Ser Gly Ala
            20                  25
```

<210> SEQ ID NO 8
<211> LENGTH: 17
<212> TYPE: PRT
<213> ORGANISM: Artificial Sequence
<220> FEATURE:
<223> OTHER INFORMATION: PSMGFR related sequence

<400> SEQUENCE: 8

```
Asp Val Ser Val Ser Asp Val Pro Phe Pro Phe Ser Ala Gln Ser Gly
1               5                   10                  15

Ala
```

<210> SEQ ID NO 9
<211> LENGTH: 35
<212> TYPE: PRT

```
<213> ORGANISM: Artificial Sequence
<220> FEATURE:
<223> OTHER INFORMATION: PSMGFR related sequence

<400> SEQUENCE: 9

Val Val Gln Leu Thr Leu Ala Phe Arg Glu Gly Thr Ile Asn Val His
1               5                   10                  15

Asp Val Glu Thr Gln Phe Asn Gln Tyr Lys Thr Glu Ala Ala Ser Arg
            20                  25                  30

Tyr Asn Leu
        35

<210> SEQ ID NO 10
<211> LENGTH: 25
<212> TYPE: PRT
<213> ORGANISM: Artificial Sequence
<220> FEATURE:
<223> OTHER INFORMATION: PSMGFR related sequence

<400> SEQUENCE: 10

Gly Thr Ile Asn Val His Asp Val Glu Thr Gln Phe Asn Gln Tyr Lys
1               5                   10                  15

Thr Glu Ala Ala Ser Arg Tyr Asn Leu
            20                  25

<210> SEQ ID NO 11
<211> LENGTH: 15
<212> TYPE: PRT
<213> ORGANISM: Artificial Sequence
<220> FEATURE:
<223> OTHER INFORMATION: PSMGFR related sequence

<400> SEQUENCE: 11

Gly Thr Ile Asn Val His Asp Val Glu Thr Gln Phe Asn Gln Tyr
1               5                   10                  15

<210> SEQ ID NO 12
<211> LENGTH: 390
<212> TYPE: DNA
<213> ORGANISM: Artificial Sequence
<220> FEATURE:
<223> OTHER INFORMATION: MIN-C2 Heavy chain variable region

<400> SEQUENCE: 12
gaggtccagc tggaggagtc agggggaggc ttagtgaagc ctggagggtc cctgaaactc      60
tcctgtgcag cctctggatt cactttcagt ggctatgcca tgtcttgggt tcgccagact     120
ccggagaaga ggctggagtg ggtcgcaacc attagtagtg gtggtactta tatctactat     180
ccagacagtg tgaaggggcg attcaccatc tccagagaca tgccaagaa caccctgtac      240
ctgcaaatga gcagtctgag gtctgaggac acggccatgt attactgtgc aagacttggg     300
ggggataatt actacgaata cttcgatgtc tggggcgcag gaccacggt caccgtctcc      360
tccgccaaaa cgacaccccc atctgtctat                                      390

<210> SEQ ID NO 13
<211> LENGTH: 130
<212> TYPE: PRT
<213> ORGANISM: Artificial Sequence
<220> FEATURE:
<223> OTHER INFORMATION: MIN-C2 Heavy chain variable region

<400> SEQUENCE: 13

Glu Val Gln Leu Glu Glu Ser Gly Gly Gly Leu Val Lys Pro Gly Gly
```

```
             1               5                  10                 15
            Ser Leu Lys Leu Ser Cys Ala Ala Ser Gly Phe Thr Phe Ser Gly Tyr
                        20                  25                  30

Ala Met Ser Trp Val Arg Gln Thr Pro Glu Lys Arg Leu Glu Trp Val
                        35                  40                  45

Ala Thr Ile Ser Ser Gly Gly Thr Tyr Ile Tyr Tyr Pro Asp Ser Val
                        50                  55                  60

Lys Gly Arg Phe Thr Ile Ser Arg Asp Asn Ala Lys Asn Thr Leu Tyr
             65                 70                  75                  80

Leu Gln Met Ser Ser Leu Arg Ser Glu Asp Thr Ala Met Tyr Tyr Cys
                        85                  90                  95

Ala Arg Leu Gly Gly Asp Asn Tyr Tyr Glu Tyr Phe Asp Val Trp Gly
                        100                 105                 110

Ala Gly Thr Thr Val Thr Val Ser Ser Ala Lys Thr Thr Pro Pro Ser
                        115                 120                 125

Val Tyr
                130
```

<210> SEQ ID NO 14
<211> LENGTH: 360
<212> TYPE: DNA
<213> ORGANISM: Artificial Sequence
<220> FEATURE:
<223> OTHER INFORMATION: MIN-C2 Kappa chain variable region

<400> SEQUENCE: 14

```
gacattgtga tcacacagtc tacagcttcc ttaggtgtat ctctggggca gagggccacc    60
atctcatgca gggccagcaa agtgtcagt acatctggct atagttatat gcactggtac   120
caacagagac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgcaacctat tactgtcagc acagtaggga gcttccgttc   300
acgttcggag gggggaccaa gctggagata aaacgggctg atgctgcacc aactgtatcc   360
```

<210> SEQ ID NO 15
<211> LENGTH: 120
<212> TYPE: PRT
<213> ORGANISM: Artificial Sequence
<220> FEATURE:
<223> OTHER INFORMATION: MIN-C2 Kappa chain variable region

<400> SEQUENCE: 15

```
            Asp Ile Val Ile Thr Gln Ser Thr Ala Ser Leu Gly Val Ser Leu Gly
             1               5                  10                 15

Gln Arg Ala Thr Ile Ser Cys Arg Ala Ser Lys Ser Val Ser Thr Ser
                        20                  25                  30

Gly Tyr Ser Tyr Met His Trp Tyr Gln Gln Arg Pro Gly Gln Pro Pro
                        35                  40                  45

Lys Leu Leu Ile Tyr Leu Ala Ser Asn Leu Glu Ser Gly Val Pro Ala
                        50                  55                  60

Arg Phe Ser Gly Ser Gly Ser Gly Thr Asp Phe Thr Leu Asn Ile His
             65                 70                  75                  80

Pro Val Glu Glu Glu Asp Ala Ala Thr Tyr Tyr Cys Gln His Ser Arg
                        85                  90                  95

Glu Leu Pro Phe Thr Phe Gly Gly Gly Thr Lys Leu Glu Ile Lys Arg
                        100                 105                 110
```

Ala Asp Ala Ala Pro Thr Val Ser
        115                 120

<210> SEQ ID NO 16
<211> LENGTH: 393
<212> TYPE: DNA
<213> ORGANISM: Artificial Sequence
<220> FEATURE:
<223> OTHER INFORMATION: MIN-E6 Heavy chain-7 variable region

<400> SEQUENCE: 16
gaggttaagc tggaggagtc tgggggagac ttagtgaagc ctggagggtc cctgaaactc      60
tcctgtgcag cctctggatt cactttcagt agatatggca tgtcttgggt tcgccagact     120
ccagacaaga ggctggagtg ggtcgcaacc attagtagtg gtggtactta catctactat     180
ccagacagtg tgaaggggcg attcaccatc tccagagaca tgccaagaa caccctgtac     240
ctgcaaatga gcagtctgaa gtctgaggac acagccatgt attactgtgc aagggataac     300
tacggtagta gctacgacta tgctatggac tactggggtc aaggaacctc agtcaccgtc     360
tcctcagcca aacaacagc cccatcggtc tat                                   393

<210> SEQ ID NO 17
<211> LENGTH: 131
<212> TYPE: PRT
<213> ORGANISM: Artificial Sequence
<220> FEATURE:
<223> OTHER INFORMATION: MIN-E6 Heavy chain-7 variable region

<400> SEQUENCE: 17

Glu Val Lys Leu Glu Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Asn Tyr Gly Ser Ser Tyr Asp Tyr Ala Met Asp Tyr Trp
            100                 105                 110

Gly Gln Gly Thr Ser Val Thr Val Ser Ser Ala Lys Thr Thr Ala Pro
        115                 120                 125

Ser Val Tyr
    130

<210> SEQ ID NO 18
<211> LENGTH: 456
<212> TYPE: DNA
<213> ORGANISM: Artificial Sequence
<220> FEATURE:
<223> OTHER INFORMATION: MIN-E6 Heavy chain-8 variable region

<400> SEQUENCE: 18
gaggtaaagc tggaggagtc tgggggagac ttagtgaagc ctggagggtc cctgaaactc      60
tcctgtgtag tctctggatt cactttcagt agatatggca tgtcttgggt tcgccagact     120
ccaggcaaga ggctggagtg ggtcgcaacc attagtggtg gcggtactta catctactat     180

```
ccagacagtg tgaaggggcg attcaccatc tccagagaca atgccaagaa caccctgtac    240
ctgcaaatga gcagtctgaa gtctgaggac acagccatgt atcactgtac aagggataac    300
tacggtagga actacgacta cggtatggac tactggggtc aaggaacctc agtcaccgtc    360
tcctcagcca aaacaacagc cccatcggtc tatccactgg ccctgtgtg tggagataca     420 actggctcct cggtgactct aggatgcctg gtcaag                              456

<210> SEQ ID NO 19
<211> LENGTH: 152
<212> TYPE: PRT
<213> ORGANISM: Artificial Sequence
<220> FEATURE:
<223> OTHER INFORMATION: MIN-E6 Heavy chain-8 variable region

<400> SEQUENCE: 19

Glu Val Lys Leu Glu Glu Ser Gly Gly Asp Leu Val Lys Pro Gly Gly
1               5                   10                  15

Ser Leu Lys Leu Ser Cys Val Val Ser Gly Phe Thr Phe Ser Arg Tyr
            20                  25                  30

Gly Met Ser Trp Val Arg Gln Thr Pro Gly Lys Arg Leu Glu Trp Val
        35                  40                  45

Ala Thr Ile Ser Gly Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr His Cys
                85                  90                  95

Thr Arg Asp Asn Tyr Gly Arg Asn Tyr Asp Tyr Gly Met Asp Tyr Trp
            100                 105                 110

Gly Gln Gly Thr Ser Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys
145                 150

<210> SEQ ID NO 20
<211> LENGTH: 345
<212> TYPE: DNA
<213> ORGANISM: Artificial Sequence
<220> FEATURE:
<223> OTHER INFORMATION: MIN-E6 Kappa chain variable region

<400> SEQUENCE: 20
gatattgtga tcacccagac tacagcaatc atgtctgcat ctccagggga ggaggtcacc     60
ctaacctgca gtgccacctc aagtgtaagt tacatacact ggttccagca gaggccaggc   120
acttctccca aactctggat ttatagcaca tccaacctgg cttctggagt ccctgttcgc   180
ttcagtggca gtggatatgg gacctcttac tctctcacaa tcagccgaat ggaggctgaa   240
gatgctgcca cttattactg ccagcaaagg agtagttccc cattcacgtt cggctcgggg   300
acaaagttgg aaataaaacg gctgatgct gcaccaactg tatcc                    345

<210> SEQ ID NO 21
<211> LENGTH: 115
<212> TYPE: PRT
<213> ORGANISM: Artificial Sequence
<220> FEATURE:
```

<223> OTHER INFORMATION: MIN-E6 Kappa chain variable region

<400> SEQUENCE: 21

Asp Ile Val Ile Thr Gln Thr Thr Ala Ile Met Ser Ala Ser Pro Gly
1               5                   10                  15

Glu Glu Val Thr Leu Thr Cys Ser Ala Thr Ser Ser Val Ser Tyr Ile
            20                  25                  30

His Trp Phe Gln Gln Arg Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Tyr Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Ser Pro Phe Thr
                85                  90                  95

Phe Gly Ser Gly Thr Lys Leu Glu Ile Lys Arg Ala Asp Ala Ala Pro
            100                 105                 110

Thr Val Ser
        115

<210> SEQ ID NO 22
<211> LENGTH: 639
<212> TYPE: DNA
<213> ORGANISM: Artificial Sequence
<220> FEATURE:
<223> OTHER INFORMATION: MIN-C2 Fab Heavy chain

<400> SEQUENCE: 22
gaggtccagc tggaggagtc tgggggaggc ttagtgaagc ctggagggtc cctgaaactc      60
tcctgtgcag cctctggatt cactttcagt ggctatgcca tgtcttgggt tcgccagact     120
ccggagaaga ggctggagtg gtcgcaacc attagtagtg gtggtactta tatctactat     180
ccagacagtg tgaaggggcg attcaccatc tccagagaca tgccaagaa caccctgtac     240 ctgcaaatga gcagtctgag gtctgaggac acggccatgt attactgtgc aagacttggg     300
ggggataatt actacgaata cttcgatgtc tggggcgcag ggaccacggt caccgtctcc     360
tccgccaaaa cgacaccccc atctgtctat ccactggccc ctggatctgc tgcccaaact     420
aactccatgg tgaccctggg atgcctggtc aagggctatt ccctgagcc agtgacagtg     480 acctggaact ctggatccct gtccagcggt gtgcacacct cccagctgt cctgcagtct     540 gacctctaca ctctgagcag ctcagtgact gtccccctcca gcacctggcc cagcgagacc     600
gtcacctgca acgttgccca cccagccagc aggaccgcg                             639

<210> SEQ ID NO 23
<211> LENGTH: 654
<212> TYPE: DNA
<213> ORGANISM: Artificial Sequence
<220> FEATURE:
<223> OTHER INFORMATION: MIN-C2 Fab Kappa chain

<400> SEQUENCE: 23
gacattgtga tcacacagtc tacagcttcc ttaggtgtat ctctggggca gagggccacc      60
atctcatgca gggccagcaa aagtgtcagt acatctggct atagttatat gcactggtac     120
caacagagac caggacagcc acccaaactc ctcatctatc ttgcatccaa cctagaatct     180
ggggtccctg ccaggttcag tggcagtggg tctgggacag acttcaccct caacatccat     240
cctgtggagg aggaggatgc tgcaacctat tactgtcagc acagtaggga gcttccgttc     300

```
acgttcggag gggggaccaa gctggagata aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc    600 actcacaaga catcaacttc acccattgtc aagagcttca acaggaatga gtgt          654
```

<210> SEQ ID NO 24
<211> LENGTH: 213
<212> TYPE: PRT
<213> ORGANISM: Artificial Sequence
<220> FEATURE:
<223> OTHER INFORMATION: MIN-C2 Fab Heavy chain
<400> SEQUENCE: 24

```
Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Leu Gly Gly Asp Asn Tyr Tyr Glu Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Arg Thr Ala
    210
```

<210> SEQ ID NO 25
<211> LENGTH: 218
<212> TYPE: PRT
<213> ORGANISM: Artificial Sequence
<220> FEATURE:
<223> OTHER INFORMATION: MIN-C2 Fab Kappa chain
<400> SEQUENCE: 25

```
Asp Ile Val Ile Thr Gln Ser Thr Ala Ser Leu Gly Val Ser Leu Gly
1               5                   10                  15

Gln Arg Ala Thr Ile Ser Cys Arg Ala Ser Lys Ser Val Ser Thr Ser
```

```
                    20                  25                  30
Gly Tyr Ser Tyr Met His Trp Tyr Gln Gln Arg Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 26
<211> LENGTH: 107
<212> TYPE: PRT
<213> ORGANISM: Artificial Sequence
<220> FEATURE:
<223> OTHER INFORMATION: MIN-C2 light CL region amino acid sequence

<400> SEQUENCE: 26

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
35                  40                  45

Gln Asn Gly Val Leu Asn Ser Trp Thr Asp Gln Asp Ser Lys Asp Ser
50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
            85                  90                  95

Pro Ile Val Lys Ser Phe Asn Arg Asn Glu Cys
        100                 105

<210> SEQ ID NO 27
<211> LENGTH: 106
<212> TYPE: PRT
<213> ORGANISM: Artificial Sequence
<220> FEATURE:
<223> OTHER INFORMATION: MIN-C2 heavy chain CH1 region amino acid
      sequence

<400> SEQUENCE: 27
```

```
Phe Asp Val Trp Gly Ala Gly Thr Thr Val Thr Val Ser Ser Ala Lys
1               5                   10                  15

Thr Thr Pro Pro Ser Val Tyr Pro Leu Ala Pro Gly Ser Ala Ala Gln
            20                  25                  30

Thr Asn Ser Met Val Thr Leu Gly Cys Leu Val Lys Gly Tyr Phe Pro
        35                  40                  45

Glu Pro Val Thr Val Thr Trp Asn Ser Gly Ser Leu Ser Ser Gly Val
    50                  55                  60

His Thr Phe Pro Ala Val Leu Gln Ser Asp Leu Tyr Thr Leu Ser Ser
65              70                  75                  80

Ser Val Thr Val Pro Ser Ser Thr Trp Pro Ser Glu Val Thr Cys
                85                  90                  95

Asn Val Ala His Pro Ala Ser Arg Thr Ala
            100                 105
```

<210> SEQ ID NO 28
<211> LENGTH: 23
<212> TYPE: PRT
<213> ORGANISM: Artificial Sequence
<220> FEATURE:
<223> OTHER INFORMATION: MIN-C2 light chain variable framework region 1
      (FWR1) amino acid sequence

<400> SEQUENCE: 28

```
Asp Ile Val Ile Thr Gln Ser Thr Ala Ser Leu Gly Val Ser Leu Gly
1               5                   10                  15

Gln Arg Ala Thr Ile Ser Cys
            20
```

<210> SEQ ID NO 29
<211> LENGTH: 23
<212> TYPE: PRT
<213> ORGANISM: Artificial Sequence
<220> FEATURE:
<223> OTHER INFORMATION: MIN-E6 light chain variable framework region 1
      (FWR1) amino acid sequence

<400> SEQUENCE: 29

```
Asp Ile Val Ile Thr Gln Thr Thr Ala Ile Met Ser Ala Ser Pro Gly
1               5                   10                  15

Glu Glu Val Thr Leu Thr Cys
            20
```

<210> SEQ ID NO 30
<211> LENGTH: 15
<212> TYPE: PRT
<213> ORGANISM: Artificial Sequence
<220> FEATURE:
<223> OTHER INFORMATION: MIN-C2 light chain variable complementarity
      determining region 1 (CDR1) amino acid sequence

<400> SEQUENCE: 30

```
Arg Ala Ser Lys Ser Val Ser Thr Ser Gly Tyr Ser Tyr Met His
1               5                   10                  15
```

<210> SEQ ID NO 31
<211> LENGTH: 10
<212> TYPE: PRT
<213> ORGANISM: Artificial Sequence
<220> FEATURE:
<223> OTHER INFORMATION: MIN-E6 light chain variable complementarity
      determining region 1 (CDR1) amino acid sequence

```
<400> SEQUENCE: 31

Ser Ala Thr Ser Ser Val Ser Tyr Ile His
1               5                   10

<210> SEQ ID NO 32
<211> LENGTH: 15
<212> TYPE: PRT
<213> ORGANISM: Artificial Sequence
<220> FEATURE:
<223> OTHER INFORMATION: MIN-C2 light chain variable framework region 2
      (FWR2) amino acid sequence

<400> SEQUENCE: 32

Trp Tyr Gln Gln Arg Pro Gly Gln Pro Pro Lys Leu Leu Ile Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: MIN-E6 light chain variable framework region 2
      (FWR2) amino acid sequence

<400> SEQUENCE: 33

Trp Phe Gln Gln Arg Pro Gly Thr Ser Pro Lys Leu Trp Ile Tyr
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: MIN-C2 light chain variable complementarity
      determining region 2 (CDR2) amino acid sequence

<400> SEQUENCE: 34

Leu Ala Ser Asn Leu Glu Ser
1               5

<210> SEQ ID NO 35
<211> LENGTH: 7
<212> TYPE: PRT
<213> ORGANISM: Artificial Sequence
<220> FEATURE:
<223> OTHER INFORMATION: MIN-E6 light chain variable complementarity
      determining region 2 (CDR2) amino acid sequence

<400> SEQUENCE: 35

Ser Thr Ser Asn Leu Ala Ser
1               5

<210> SEQ ID NO 36
<211> LENGTH: 32
<212> TYPE: PRT
<213> ORGANISM: Artificial Sequence
<220> FEATURE:
<223> OTHER INFORMATION: MIN-C2 light chain variable framework region 3
      (FWR3) amino acid sequence

<400> SEQUENCE: 36

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30
```

```
<210> SEQ ID NO 37
<211> LENGTH: 32
<212> TYPE: PRT
<213> ORGANISM: Artificial Sequence
<220> FEATURE:
<223> OTHER INFORMATION: MIN-E6 light chain variable framework region 3
      (FWR3) amino acid sequence

<400> SEQUENCE: 37

Gly Val Pro Val Arg Phe Ser Gly Ser Gly Tyr Gly Thr Ser Tyr Ser
1               5                   10                  15

Leu Thr Ile Ser Arg Met Glu Ala Glu Asp Ala Ala Thr Tyr Tyr Cys
            20                  25                  30

<210> SEQ ID NO 38
<211> LENGTH: 9
<212> TYPE: PRT
<213> ORGANISM: Artificial Sequence
<220> FEATURE:
<223> OTHER INFORMATION: MIN-C2 light chain variable complementarity
      determining region 3 (CDR3) amino acid sequence

<400> SEQUENCE: 38

Gln His Ser Arg Glu Leu Pro Phe Thr
1               5

<210> SEQ ID NO 39
<211> LENGTH: 9
<212> TYPE: PRT
<213> ORGANISM: Artificial Sequence
<220> FEATURE:
<223> OTHER INFORMATION: MIN-E6 light chain variable complementarity
      determining region 3 (CDR3) amino acid sequence

<400> SEQUENCE: 39

Gln Gln Arg Ser Ser Ser Pro Phe Thr
1               5

<210> SEQ ID NO 40
<211> LENGTH: 30
<212> TYPE: PRT
<213> ORGANISM: Artificial Sequence
<220> FEATURE:
<223> OTHER INFORMATION: MIN-C2 heavy chain variable framework region 1
      (FWR1) amino acid sequence

<400> SEQUENCE: 40

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: MIN-E6-7 heavy chain variable framework region
      1 (FWR1) amino acid sequence

<400> SEQUENCE: 41

Glu Val Lys Leu Glu Glu Ser Gly Gly Asp Leu Val Lys Pro Gly Gly
1               5                   10                  15

Ser Leu Lys Leu Ser Cys Ala Ala Ser Gly Phe Thr Phe Ser
            20                  25                  30
```

-continued

```
<210> SEQ ID NO 42
<211> LENGTH: 30
<212> TYPE: PRT
<213> ORGANISM: Artificial Sequence
<220> FEATURE:
<223> OTHER INFORMATION: MIN-E6-8 heavy chain variable framework region
      1 (FWR1) amino acid sequence

<400> SEQUENCE: 42

Glu Val Lys Leu Glu Glu Ser Gly Gly Asp Leu Val Lys Pro Gly Gly
1               5                   10                  15

Ser Leu Lys Leu Ser Cys Val Val Ser Gly Phe Thr Phe Ser
            20                  25                  30

<210> SEQ ID NO 43
<211> LENGTH: 5
<212> TYPE: PRT
<213> ORGANISM: Artificial Sequence
<220> FEATURE:
<223> OTHER INFORMATION: MIN-C2 heavy chain variable complementarity
      determining region 1 (CDR1) amino acid sequence

<400> SEQUENCE: 43

Gly Tyr Ala Met Ser
1               5

<210> SEQ ID NO 44
<211> LENGTH: 5
<212> TYPE: PRT
<213> ORGANISM: Artificial Sequence
<220> FEATURE:
<223> OTHER INFORMATION: MIN-E6-7 heavy chain variable complementarity
      determining region 1 (CDR1) amino acid sequence

<400> SEQUENCE: 44

Arg Tyr Gly Met Ser
1               5

<210> SEQ ID NO 45
<211> LENGTH: 5
<212> TYPE: PRT
<213> ORGANISM: Artificial Sequence
<220> FEATURE:
<223> OTHER INFORMATION: MIN-E6-8 heavy chain variable complementarity
      determining region 1 (CDR1) amino acid sequence

<400> SEQUENCE: 45

Arg Tyr Gly Met Ser
1               5

<210> SEQ ID NO 46
<211> LENGTH: 14
<212> TYPE: PRT
<213> ORGANISM: Artificial Sequence
<220> FEATURE:
<223> OTHER INFORMATION: MIN-C2 heavy chain variable framework region 2
      (FWR2) amino acid sequence

<400> SEQUENCE: 46

Trp Val Arg Gln Thr Pro Glu Lys Arg Leu Glu Trp Val Ala
1               5                   10

<210> SEQ ID NO 47
<211> LENGTH: 14
<212> TYPE: PRT
<213> ORGANISM: Artificial Sequence
<220> FEATURE:
<223> OTHER INFORMATION: MIN-E6-7 heavy chain variable framework region
```

2 (FWR2) amino acid sequence

<400> SEQUENCE: 47

Trp Val Arg Gln Thr Pro Asp Lys Arg Leu Glu Trp Val Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: MIN-E6-8 heavy chain variable framework region
      2 (FWR2) amino acid sequence

<400> SEQUENCE: 48

Trp Val Arg Gln Thr Pro Gly Lys Arg Leu Glu Trp Val Ala
1               5                   10

<210> SEQ ID NO 49
<211> LENGTH: 17
<212> TYPE: PRT
<213> ORGANISM: Artificial Sequence
<220> FEATURE:
<223> OTHER INFORMATION: MIN-C2 heavy chain variable complementarity
      determining region 2 (CDR2) amino acid sequence

<400> SEQUENCE: 49

Thr Ile Ser Ser Gly Gly Thr Tyr Ile Tyr Tyr Pro Asp Ser Val Lys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: MIN-E6-7 heavy chain variable complementarity
      determining region 2 (CDR2) amino acid sequence

<400> SEQUENCE: 50

Thr Ile Ser Ser Gly Gly Thr Tyr Ile Tyr Tyr Pro Asp Ser Val Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: MIN-E6-8 heavy chain variable complementarity
      determining region 2 (CDR2) amino acid sequence

<400> SEQUENCE: 51

Thr Ile Ser Gly Gly Gly Thr Tyr Ile Tyr Tyr Pro Asp Ser Val Lys
1               5                   10                  15

Gly

<210> SEQ ID NO 52
<211> LENGTH: 32
<212> TYPE: PRT
<213> ORGANISM: Artificial Sequence
<220> FEATURE:
<223> OTHER INFORMATION: MIN-C2 heavy chain variable framework region 3
      (FWR3) amino acid sequence

<400> SEQUENCE: 52

Arg Phe Thr Ile Ser Arg Asp Asn Ala Lys Asn Thr Leu Tyr Leu Gln
1               5                   10                  15

Met Ser Ser Leu Arg Ser Glu Asp Thr Ala Met Tyr Tyr Cys Ala Arg
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: MIN-E6-7 heavy chain variable framework region
      3 (FWR3) amino acid sequence

<400> SEQUENCE: 53

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Arg
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: MIN-E6-8 heavy chain variable framework region
      3 (FWR3) amino acid sequence

<400> SEQUENCE: 54

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr His Cys Thr Arg
            20                  25                  30

<210> SEQ ID NO 55
<211> LENGTH: 9
<212> TYPE: PRT
<213> ORGANISM: Artificial Sequence
<220> FEATURE:
<223> OTHER INFORMATION: MIN-C2 heavy chain variable complementarity
      determining region 3 (CDR3) amino acid sequence

<400> SEQUENCE: 55

Leu Gly Gly Asp Asn Tyr Tyr Glu Tyr
1               5

<210> SEQ ID NO 56
<211> LENGTH: 10
<212> TYPE: PRT
<213> ORGANISM: Artificial Sequence
<220> FEATURE:
<223> OTHER INFORMATION: MIN-E6-7 heavy chain variable complementarity
      determining region 3 (CDR3) amino acid sequence

<400> SEQUENCE: 56

Asp Asn Tyr Gly Ser Ser Tyr Asp Tyr Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: MIN-E6-8 heavy chain variable complementarity
      determining region 3 (CDR3) amino acid sequence

<400> SEQUENCE: 57

```
Asp Asn Tyr Gly Arg Asn Tyr Asp Tyr Gly
1               5                   10
```

<210> SEQ ID NO 58
<211> LENGTH: 30
<212> TYPE: PRT
<213> ORGANISM: Artificial Sequence
<220> FEATURE:
<223> OTHER INFORMATION: IGHV3 (name from Igblast): FWR1: Human IgG
      antibody framework region sequence with 84.7% homology (249/294)
      to variable heavy chain region of MIN-C2

<400> SEQUENCE: 58

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 59
<211> LENGTH: 14
<212> TYPE: PRT
<213> ORGANISM: Artificial Sequence
<220> FEATURE:
<223> OTHER INFORMATION: IGHV3 (name from Igblast): FWR2: Human IgG
      antibody framework region sequence with 84.7% homology (249/294)
      to variable heavy chain region of MIN-C2

<400> SEQUENCE: 59

```
Trp Val Arg Gln Ala Pro Gly Lys Gly Leu Glu Trp Val Ser
1               5                   10
```

<210> SEQ ID NO 60
<211> LENGTH: 27
<212> TYPE: PRT
<213> ORGANISM: Artificial Sequence
<220> FEATURE:
<223> OTHER INFORMATION: IGHV3 (name from Igblast): FWR3: Human IgG
      antibody framework region sequence with 84.7% homology (249/294)
      to variable heavy chain region of MIN-C2

<400> SEQUENCE: 60

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val
            20                  25
```

<210> SEQ ID NO 61
<211> LENGTH: 23
<212> TYPE: PRT
<213> ORGANISM: Artificial Sequence
<220> FEATURE:
<223> OTHER INFORMATION: IGkV7 (name from Igblast): FWR1: Human IgG
      antibody framework region sequence with 76.4% homology (226/296)
      to variable light chain region of MIN-C2

<400> SEQUENCE: 61

```
Asp Ile Val Leu Thr Gln Ser Pro Ala Ser Leu Ala Val Ser Pro Gly
1               5                   10                  15

Gln Arg Ala Thr Ile Thr Cys
            20
```

<210> SEQ ID NO 62
<211> LENGTH: 15
<212> TYPE: PRT
<213> ORGANISM: Artificial Sequence
<220> FEATURE:

```
<223> OTHER INFORMATION: IGkV7 (name from Igblast): FWR2: Human IgG
      antibody framework region sequence with 76.4% homology (226/296)
      to variable light chain region of MIN-C2

<400> SEQUENCE: 62

Trp Tyr Gln Gln Lys Pro Gly Gln Pro Pro Lys Leu Leu Ile Tyr
1               5                   10                  15

<210> SEQ ID NO 63
<211> LENGTH: 31
<212> TYPE: PRT
<213> ORGANISM: Artificial Sequence
<220> FEATURE:
<223> OTHER INFORMATION: IGkV7 (name from Igblast): FWR 3: Human IgG
      antibody framework region sequence with 76.4% homology (226/296)
      to variable light chain region of MIN-C2

<400> SEQUENCE: 63

Gly Val Pro Ala Arg Phe Ser Gly Ser Gly Ser Gly Thr Asp Phe Thr
1               5                   10                  15

Leu Thr Ile Asn Pro Val Glu Ala Asn Asp Thr Ala Asn Tyr Tyr
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: IGHV3 (name from Igblast): FWR1: Human IgG
      antibody framework region sequence with 84.1% homology (249/296)
      to variable heavy chain region of MIN-E6

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 65
<211> LENGTH: 14
<212> TYPE: PRT
<213> ORGANISM: Artificial Sequence
<220> FEATURE:
<223> OTHER INFORMATION: IGHV3 (name from Igblast): FWR2: Human IgG
      antibody framework region sequence with 84.1% homology (249/296)
      to variable heavy chain region of MIN-E6

<400> SEQUENCE: 65

Trp Val Arg Gln Ala Pro Gly Lys Gly Leu Glu Trp Val Ser
1               5                   10

<210> SEQ ID NO 66
<211> LENGTH: 32
<212> TYPE: PRT
<213> ORGANISM: Artificial Sequence
<220> FEATURE:
<223> OTHER INFORMATION: IGHV3 (name from Igblast): FWR3: Human IgG
      antibody framework region sequence with 84.1% homology (249/296)
      to variable heavy chain region of MIN-E6

<400> SEQUENCE: 66

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30
```

```
<210> SEQ ID NO 67
<211> LENGTH: 23
<212> TYPE: PRT
<213> ORGANISM: Artificial Sequence
<220> FEATURE:
<223> OTHER INFORMATION: IGkV3 (name from Igblast): FWR1: Human IgG
      antibody framework region sequence with 69.5% homology (187/269)
      to variable light chain region of MIN-E6

<400> SEQUENCE: 67

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 68
<211> LENGTH: 15
<212> TYPE: PRT
<213> ORGANISM: Artificial Sequence
<220> FEATURE:
<223> OTHER INFORMATION: IGkV3 (name from Igblast): FWR2: Human IgG
      antibody framework region sequence with 69.5% homology (187/269)
      to variable light chain region of MIN-E6

<400> SEQUENCE: 68

Trp Phe Gln Gln Arg Pro Gly Thr Ser Pro Lys Leu Leu Ile Tyr
1               5                   10                  15

<210> SEQ ID NO 69
<211> LENGTH: 32
<212> TYPE: PRT
<213> ORGANISM: Artificial Sequence
<220> FEATURE:
<223> OTHER INFORMATION: IGkV3 (name from Igblast): FWR3: Human IgG
      antibody framework region sequence with 69.5% homology (187/269)
      to variable light chain region of MIN-E6

<400> SEQUENCE: 69

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 70
<211> LENGTH: 19
<212> TYPE: PRT
<213> ORGANISM: Artificial Sequence
<220> FEATURE:
<223> OTHER INFORMATION: 2D6C3 Kappa Chain Variable Region

<400> SEQUENCE: 70

Cys Asp Arg Arg Ser Ser Gln Thr Ile Val His Ser Asn Gly Asn Thr
1               5                   10                  15

Tyr Leu Glu

<210> SEQ ID NO 71
<211> LENGTH: 10
<212> TYPE: PRT
<213> ORGANISM: Artificial Sequence
<220> FEATURE:
<223> OTHER INFORMATION: 2D6C3 Kappa Chain Variable Region

<400> SEQUENCE: 71

Cys Asp Arg Lys Val Ser Asn Arg Phe Ser
1               5                   10
```

```
<210> SEQ ID NO 72
<211> LENGTH: 12
<212> TYPE: PRT
<213> ORGANISM: Artificial Sequence
<220> FEATURE:
<223> OTHER INFORMATION: 2D6C3 Kappa Chain Variable Region

<400> SEQUENCE: 72

Cys Asp Arg Phe Gln Gly Ser His Val Pro Phe Thr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: 2D6C3 Heavy Chain Variable Region

<400> SEQUENCE: 73

Cys Asp Arg Gly Tyr Ala Met Ser
1               5

<210> SEQ ID NO 74
<211> LENGTH: 20
<212> TYPE: PRT
<213> ORGANISM: Artificial Sequence
<220> FEATURE:
<223> OTHER INFORMATION: 2D6C3 Heavy Chain Variable Region

<400> SEQUENCE: 74

Cys Asp Arg Thr Ile Ser Ser Gly Gly Thr Tyr Ile Tyr Tyr Pro Asp
1               5                   10                  15

Ser Val Lys Gly
            20

<210> SEQ ID NO 75
<211> LENGTH: 12
<212> TYPE: PRT
<213> ORGANISM: Artificial Sequence
<220> FEATURE:
<223> OTHER INFORMATION: 2D6C3 Heavy Chain Variable Region

<400> SEQUENCE: 75

Cys Asp Arg Leu Gly Gly Asp Asn Tyr Tyr Glu Tyr
1               5                   10

<210> SEQ ID NO 76
<211> LENGTH: 18
<212> TYPE: PRT
<213> ORGANISM: Artificial Sequence
<220> FEATURE:
<223> OTHER INFORMATION: 2D6C8 Kappa Chain Variable Region

<400> SEQUENCE: 76

Cys Asp Arg Arg Ala Ser Lys Ser Val Ser Thr Ser Gly Tyr Ser Tyr
1               5                   10                  15

Met His

<210> SEQ ID NO 77
<211> LENGTH: 10
<212> TYPE: PRT
<213> ORGANISM: Artificial Sequence
<220> FEATURE:
<223> OTHER INFORMATION: 2D6C8 Kappa Chain Variable Region

<400> SEQUENCE: 77
```

Cys Asp Arg Leu Val Ser Asn Leu Glu Ser
1               5                   10

<210> SEQ ID NO 78
<211> LENGTH: 13
<212> TYPE: PRT
<213> ORGANISM: Artificial Sequence
<220> FEATURE:
<223> OTHER INFORMATION: 2D6C8 Kappa Chain Variable Region

<400> SEQUENCE: 78

Cys Asp Arg Gln His Ile Arg Glu Leu Thr Arg Ser Glu
1               5                   10

<210> SEQ ID NO 79
<211> LENGTH: 8
<212> TYPE: PRT
<213> ORGANISM: Artificial Sequence
<220> FEATURE:
<223> OTHER INFORMATION: 2D6C8 Heavy Chain Variable Region

<400> SEQUENCE: 79

Cys Asp Arg Gly Tyr Ala Met Ser
1               5

<210> SEQ ID NO 80
<211> LENGTH: 20
<212> TYPE: PRT
<213> ORGANISM: Artificial Sequence
<220> FEATURE:
<223> OTHER INFORMATION: 2D6C8 Heavy Chain Variable Region

<400> SEQUENCE: 80

Cys Asp Arg Thr Ile Ser Ser Gly Gly Thr Tyr Ile Tyr Tyr Pro Asp
1               5                   10                  15

Ser Val Lys Gly
            20

<210> SEQ ID NO 81
<211> LENGTH: 12
<212> TYPE: PRT
<213> ORGANISM: Artificial Sequence
<220> FEATURE:
<223> OTHER INFORMATION: 2D6C8 Heavy Chain Variable Region

<400> SEQUENCE: 81

Cys Asp Arg Leu Gly Gly Asp Asn Tyr Tyr Glu Tyr
1               5                   10

<210> SEQ ID NO 82
<211> LENGTH: 18
<212> TYPE: PRT
<213> ORGANISM: Artificial Sequence
<220> FEATURE:
<223> OTHER INFORMATION: 3C2B1 Kappa Chain Variable Region

<400> SEQUENCE: 82

Cys Asp Arg Arg Ala Ser Lys Ser Ile Ser Thr Ser Asp Tyr Asn Tyr
1               5                   10                  15

Ile His

<210> SEQ ID NO 83
<211> LENGTH: 10
<212> TYPE: PRT
<213> ORGANISM: Artificial Sequence
<220> FEATURE:

```
<223> OTHER INFORMATION: 3C2B1 Kappa Chain Variable Region

<400> SEQUENCE: 83

Cys Asp Arg Leu Ala Ser Asn Leu Glu Ser
1               5                   10

<210> SEQ ID NO 84
<211> LENGTH: 13
<212> TYPE: PRT
<213> ORGANISM: Artificial Sequence
<220> FEATURE:
<223> OTHER INFORMATION: 3C2B1 Kappa Chain Variable Region

<400> SEQUENCE: 84

Cys Asp Arg Gln His Ser Arg Glu Leu Pro Leu Thr Phe
1               5                   10

<210> SEQ ID NO 85
<211> LENGTH: 8
<212> TYPE: PRT
<213> ORGANISM: Artificial Sequence
<220> FEATURE:
<223> OTHER INFORMATION: 3C2B1 Heavy Chain Variable Region

<400> SEQUENCE: 85

Cys Asp Arg Thr Tyr Thr Met Ser
1               5

<210> SEQ ID NO 86
<211> LENGTH: 20
<212> TYPE: PRT
<213> ORGANISM: Artificial Sequence
<220> FEATURE:
<223> OTHER INFORMATION: 3C2B1 Heavy Chain Variable Region

<400> SEQUENCE: 86

Cys Asp Arg Thr Ile Ser Thr Gly Gly Asp Lys Thr Tyr Tyr Ser Asp
1               5                   10                  15

Ser Val Lys Gly
            20

<210> SEQ ID NO 87
<211> LENGTH: 13
<212> TYPE: PRT
<213> ORGANISM: Artificial Sequence
<220> FEATURE:
<223> OTHER INFORMATION: 3C2B1 Heavy Chain Variable Region

<400> SEQUENCE: 87

Cys Asp Arg Gly Thr Thr Ala Met Tyr Tyr Tyr Ala Met
1               5                   10
```

STEM CELL ENHANCING THERAPEUTICS

BACKGROUND

A problem encountered by oncologists is that they must balance the benefit of chemotherapy against the risk of killing the patient during the course of killing their cancers. One of the life-threatening side effects of chemotherapy is that cytotoxic drugs kill cancer cells but also kill healthy cells and in particular kill the patients' stem cells. Stem cells in the bone marrow are constantly regenerating to supply the body with red blood cells, which carry oxygen, white blood cells, which fight infection and platelets which cause the blood to clot. Chemo and radiation can destroy the stem cells which eventually become blood cells and thus put the patient's life at risk, which makes the physician reduce the cancer killing treatments. The problem with designing agents to counter these deleterious effects of cancer treatment is that blood cells are terminally differentiated cells—meaning that they cannot divide to replicate themselves. They developed from hematopoietic stem cells in the bone marrow. This means that it is not possible to collect some red or white blood cells from a patient and expand them in vitro then inject them back into the patient.

There are currently a handful of drugs on the market that are used to modulate stem cell development in a patient. The first group, known as erythropoiesis stimulating agents (ESAs), includes Epoetin, marketed under the trade names Procrit and Epogen, and Aranesp. These drugs are used to treat anemia in patients with chronic kidney disease and in cancer patients with chemotherapy-induced anemia. These drugs do not stimulate the growth of stem cells in the bone marrow but rather skew the development of the patient's stem cells such that more become blood cells of the erythroid lineage. Epogen and epogen-like drugs help cancer patents and chronic kidney disease patients by increasing the number of stem cells in the bone marrow that differentiate into red blood cells.

Another class of drugs that is used to stimulate the production of white blood cells. Colony-stimulating factors (CSFs) that include G-CSF (granulocyte-colony stimulating factors: marketed as Filgrastim) and GM-CSF (granulocyte-macrophage colony stimulating factors: Sargamostim marketed as Leukine) stimulate the production of the precursors of white blood cells, which can mature to become neutrophils, macrophages and dendritic cells and may be administered with or without cyclophosphamide. The CSFs are also stem cell mobilizers which cause blood cell progenitors to be secreted from the bone marrow. However, a drawback of G-CSF and GM-CSF is that they inhibit bone formation. Another mobilizer of hematopoietic stem cells is the CXCR4 antagonist AMD3100, which reportedly mobilizes blood cell progenitors without inhibiting bone formation.

Both erythropoiesis stimulating agents (ESAs) and CSFs can be used to accelerate the recovery of blood cells from effects of chemotherapy, used after bone marrow transplant, used before or after stem cell transplant which may be transplanted into the peripheral blood, and or to treat a patient who could benefit from increased production of hematopoietic stem cells or blood cells or their progenitors.

Both ESAs and CSFs function by skewing the maturation of stem cells toward the hematopoietic stem cell lineages and necessarily away from maturation into other types of cells. It follows that there may be unwanted and dangerous side effects stemming from the inhibition of other types of cells that are produced in the bone marrow. In fact, the FDA recently issued warnings that the use of Procrit, Epogen or Aranesp increases the risk of developing cancers and also increases the risk of heart attack and stroke.

Thus an improvement would be the development of agents that stimulate the production of or skew the development of stem cells to blood cell lineages via a pathway that is different from that of the ESAs and the CSFs. A greater improvement to the state of the art would be the development of agents that stimulate the production of stem cells in the bone marrow rather than just skewing their maturation in one direction. An even greater improvement to the state of the art would be the development of an agent(s) that would stimulate the growth of stem cells but would not stimulate the growth of cancer cells or increase the patient's risk of developing another cancer. A yet greater improvement would be the development of an anti-cancer agent that would kill the cancer cells without killing the patient's stem cells.

SUMMARY OF THE INVENTION

In one aspect, the present invention is directed to a method for treating a patient whose blood cells or bone marrow cells have been depleted, which may occur in some instances as a result of exposure to radiation, the method including administering to the patient a stem cell specific antibody. In another aspect, the present invention is directed to a method for treating a patient suffering from low blood cell count by stimulating the growth of hematopoietic stem cells or progenitor cells by administering to the patient a stem cell specific antibody.

In another aspect, the present invention is directed to a method of stimulating growth of bone marrow cells, hematopoietic stem or progenitor cells in vitro and then administering to a patient suffering from low blood cell count in the peripheral blood or in the bone marrow, in which the method includes administering to the patient a stem cell specific antibody.

In another aspect, the present invention is directed to a method of diagnosing cancer by testing a patient sample with an antibody that preferentially binds cancer cells compared to its binding to stem cells.

In a preferred embodiment, the cancer specific antibodies of the invention are administered to a patient whose treatment regime also includes treatment with stem cell specific antibodies.

In another aspect, the present invention is directed to a method of selecting therapeutic antibodies for the treatment of cancer involving de-selecting those antibodies that bind to stem cells. Similarly, the present invention is directed to a method of selecting therapeutic antibodies for the treatment of conditions requiring regeneration of blood cells or bone marrow cells, involving de-selecting those antibodies that bind to cancer cells.

In one aspect, the present invention is directed to a method for treating a patient who would benefit from stimulation of the patient's stem cells, comprising administering to the patient an antibody that specifically binds to an epitope of the MUC1 protein expressed on human undifferentiated stem cells. The antibody specifically may bind to at least six consecutive amino acids of the peptide of SEQ ID NO:4, SEQ ID NO:5, SEQ ID NO:6, SEQ ID NO:9, SEQ ID NO:10 or SEQ ID NO:11. In particular, the antibody may not bind to the peptide of SEQ ID NO:3, SEQ ID NO:7 or SEQ ID NO:8. The patient may suffer from cancer. The patient may suffer from cancer and is receiving chemotherapy or radiation. Or, the patient may suffer from chronic kidney disease.

In another aspect, the invention is directed to a method for treating a patient suffering from cancer or at risk of developing cancer, comprising administering to the patient an antibody that specifically binds to an epitope of the MUC1 protein that is expressed on cancer cells but is not expressed on human undifferentiated stem cells. The antibody may specifically bind to the peptide of SEQ ID NO:3 and may not bind to the peptide of SEQ ID NO:4.

In still another aspect, the invention is directed to a method for treating a patient diagnosed with a MUC1-positive cancer comprising administering to the patient a monovalent cancer cell-specific antibody.

In another aspect, the invention is directed to a method for treating a patient diagnosed with a MUC1-positive cancer comprising administering to the patient a monovalent cancer cell-specific antibody.

In another aspect, the invention is directed to a method for treating a patient diagnosed with a MUC1-positive cancer comprising administering to the patient a monovalent cancer cell-specific antibody and bivalent stem cell specific antibody.

In another aspect, the invention is directed to a method for proliferating stem or progenitor cells, comprising contacting the cells with an antibody that specifically binds to an epitope of the MUC1 protein expressed on human stem cells, without causing proliferation of cancer cells.

In yet another aspect, the invention is directed to a method of obtaining an antibody that specifically binds to stem cells, but not to cancer cells comprising the steps of:

(i) generating a mixed set of antibodies that recognize a peptide whose sequence is that of any of the peptides having sequence of SEQ ID NOS:1-11;

(ii) selecting those antibodies that bind to a peptide of SEQ ID NO:4, SEQ ID NO:5, or SEQ ID NO:6, but not to the peptide of SEQ ID NO:3;

(iii) selecting those antibodies that when adsorbed onto a surface facilitate the attachment of stem cells; and (iv) selecting those antibodies that in the bivalent form stimulate the growth of stem cells and in the monovalent form inhibit the growth of stem cells, while having no effect on cancer cells.

DESCRIPTION OF THE DRAWINGS

FIG. 2 shows titer of subclones on MUC1* and MUC1* on peptides SED ID NO:3, "N delta 10" and SEQ ID NO:4, "C delta 10".

FIG. 3 shows FACS summary of live MUC1* (+) breast cancer cells (T47D cells)—only cancer cell antibodies (C2) recognize cancer cells; stem cell antibodies (C3) do not.

FIG. 4 shows FACS summary of live MUC1* (+) breast cancer cells (1500 (ZR-75-1 cells)); monoclonal antibody C2 (MIN-C2) binds to cancer cells. C3 (2D6C3) does not bind to breast cancer cells.

FIG. 5 shows FACS summary of MUC1* (+) prostate cancer cells (DU145 cells): cancer cell antibodies C2 (MIN-C2) and E6 (MIN-E6) bind to MUC1-positive prostate cancer cells DU145; stem cell antibody C3 (2D6C3) does not.

FIG. 6 shows that stem cell antibody (C3) recognizes stem cells but not cancer cells.

FIG. 7 shows that bivalent stem cell antibodies C3 (2D6C3) and C8 (2D6C8) stimulate stem cell growth better than the natural ligand NM23.

FIG. 10 shows photographs of BGO1V/hOG embryonic stem cells growing in plates in the presence of either the control 8 nM NM23 (dimeric) or the Fab of either the cancer specific monoclonal antibody C2 (MIN-C2) or the Fab of stem cell specific monoclonal antibody C3 (2D6C3) at the concentrations indicated, showing that only the C3 Fab at 100 ug/ml significantly inhibited the growth of stem cells.

FIG. 11 shows photographs of BGO1V/hOG embryonic stem cells growing in plates in the presence of either the control 8 nM NM23 (dimeric) or the Fab of cancer specific monoclonal antibodies C2 (MIN-C2) and E6 (MIN-E6), showing that neither cancer specific antibody inhibited the growth of stem cells.

FIG. 12 shows that Fab's of the stem cell antibodies inhibit stem cell growth and cause loss of pluripotency marker Tra 1-60; here we show that the Fab's of stem cell monoclonal antibodies C3 and C8 decrease expression of stem cell marker Tra 1-60; the Fab of cancer cell antibody E6 has no effect on inhibition of BG01V cell growth: effect of Fab's measured at t=72 hrs.

FIG. 13 shows that stem cell specific mAbs (C3 and C8) do not bind to DU145 prostate cancer cells and do not inhibit cancer cell growth; Fab's of cancer specific mAbs (C2 and E6) do. The Fabs bind to and block ligand-induced dimerization of MUC1*.

FIG. 14 shows photographs and graphs of cell counts of MUC1-positive T47D breast cancer cells after treatment with either the Fab of cancer specific antibody C2 (CA-C2-Fab (MIN-C2)), Fab of E6 (CA-E6-Fab (MIN-E6)) or the Fabs of stem cell specific antibodies C3 (STEM-C3-FAB (2D6C3)) or C8 (STEM-C8-Fab (2D6C8)), showing that only the Fabs of the cancer specific antibodies inhibited the growth of cancer cells. FIG. 14 shows stem cell specific mAbs (C3 and C8) do not bind to cancer cells and do not inhibit cancer cell growth; Fabs of cancer specific mAbs (C2 and E6) do.

FIG. 15 shows photographs and graphs of cell counts of MUC1-positive DU145 prostate cancer cells after treatment with either the Fab of cancer specific antibody C2 (C2-Fab (MIN-C2)), Fab of E6 (E6-Fab (MIN-E6)) or the Fabs of stem cell specific antibodies C3 (C3-Fab (2D6C3)) or C8 (C8-Fab (2D6C8)), showing that only the Fabs of the cancer specific antibodies inhibited the growth of cancer cells.

FIG. 17 shows that human breast cancer tumors (T47D) were implanted into female Nu/Nu mice with estrogen pellets; anti-MUC1* Fab inhibited tumor growth.

FIG. 18 shows photographs of two of the mice from that study.

FIG. 19 shows anti-MUC1* Fab inhibits growth of DU145 tumors implanted into male NOD/SCID mice. miR-145 except for V8, low miR=high tumor volumes, except for Fab 5, high miR-145=low tumor volume.

FIG. 20 shows that animals treated with anti-MUC1* Fab express less MUC1* growth factor receptor post treatment and become more differentiated (miR-145 increases).

FIG. 21 shows normalized tumor growth—DU145 human prostate cancer in NOD/SCID male mice. Groups 1 and 2 tumors were very large after 27 days growth—350-550 mm$^3$ at start of treatment. Groups 3 and 4 tumors were 175-300 mm$^3$ at start of treatment. Despite size difference, both vehicle groups quickly merged to the same growth rate and size; smaller tumors responded better than the very large tumors as expected; 160 mg/kg every 48 hrs.

FIG. 22 shows photos of mice bearing human prostate tumors that received the mock treatment.

FIG. 23 shows photos of mice bearing human prostate tumors that received the cancer specific E6 (MIN-E6) Fab.

FIG. 24 shows anti-MUC1* IgG monoclonal antibody light chain variable region sequences.

FIG. 25 shows anti-MUC1* IgG monoclonal antibody heavy chain variable region sequences.

```
FIG. 28 shows amino acid sequence for the 2D6C3
Kappa Chain Variable Region.
                                        (SEQ ID NO: 70)
CDR1: RSSQTIVHSNGNTYLE;

Figure 1:
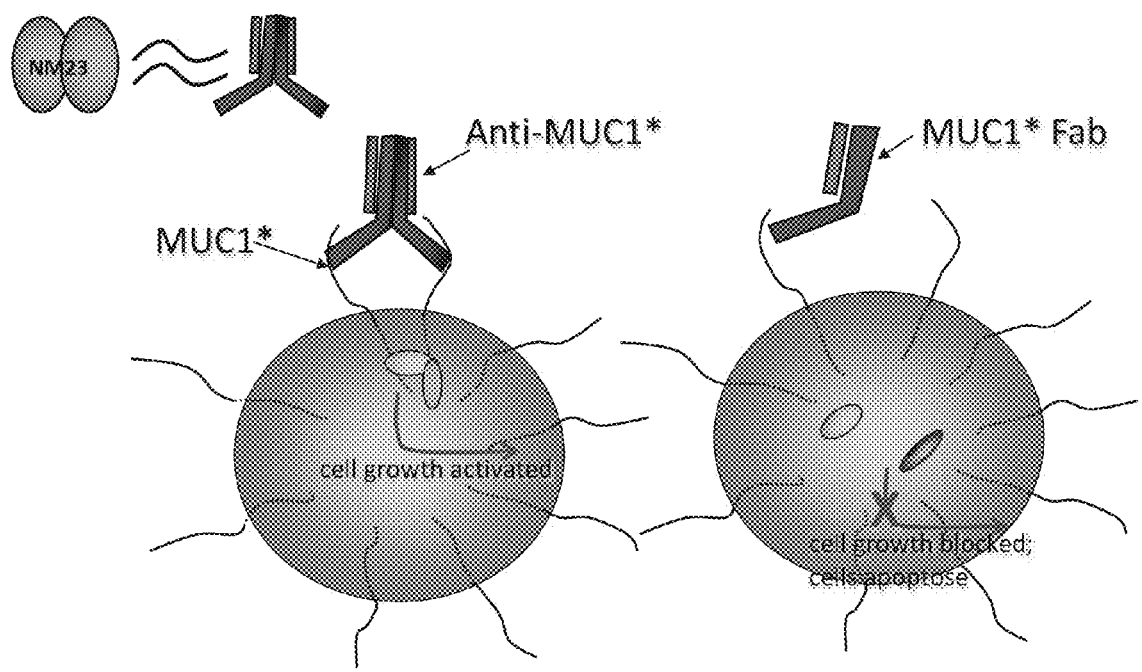
FIG. 1 is a cartoon depicting how bivalent antibodies that recognized MUC1* receptor stimulate growth, but monovalent Fabs of those antibodies inhibit growth by blocking its interaction with its cognate ligand, dimeric NM23. Bivalent antibodies mimic activity of ligand NM23 to make cancer cells or stem cells grow; monovalent Fab blocks their growth.

(SEQ ID NO: 71)
CDR2: KVSNRFS;
and (SEQ ID NO: 72)
CDR3: FQGSHVPFT.

FIG. 29 shows amino acid sequence for the 2D6C3
Heavy Chain Variable Region.
                                        (SEQ ID NO: 73)
CDR1: GYAMS;

(SEQ ID NO: 74)
CDR2: TISSGGTYIYYPDSVKG;
and (SEQ ID NO: 75)
CDR3: LGGDNYYEY.

FIG. 30 shows amino acid sequence for the 2D6C8
Kappa Chain Variable Region.
                                        (SEQ ID NO: 76)
CDR1: RASKSVSTSGYSYMH;
```

-continued

CDR2: LVSNLES;  (SEQ ID NO: 77)
and

CDR3: QHIRELTRSE.  (SEQ ID NO: 78)

FIG. 31 shows amino acid sequence for the 2D6C8
Heavy Chain Variable Region.

CDR1: GYAMS;  (SEQ ID NO: 79)

CDR2: TISSGGTYIYYPDSVKG;  (SEQ ID NO: 80)
and

CDR3: LGGDNYYEY.  (SEQ ID NO: 81)

FIG. 32 shows amino acid sequence for the 3C2B1
Kappa Chain Variable Region.

CDR1: RASKSISTSDYNYIH;  (SEQ ID NO: 82)

CDR2: LASNLES;  (SEQ ID NO: 83)
and

CDR3: QHSRELPLTF.  (SEQ ID NO: 84)

FIG. 33 shows amino acid sequence for the 3C2B1
Heavy Chain Variable Region.

CDR1: TYTMS;  (SEQ ID NO: 85)

CDR2: TISTGGDKTYYSDSVKG;  (SEQ ID NO: 86)
and

CDR3: GTTAMYYYAM.  (SEQ ID NO: 87)

DETAILED DESCRIPTION OF THE INVENTION

The present invention discloses antibodies and antibody variants that modulate a pathway involving MUC1* wherein one set of antibodies preferentially binds to MUC1* as it exists on stem cells but does not recognize MUC1* on cancer cells as well and another set of antibodies that preferentially binds to MUC1* as it exists on cancer cells but does not recognize MUC1* on stem cells as well. The present invention further discloses methods for identifying other antibodies that fall into these categories. The invention further discloses methods for using the first set of antibodies, hereafter referred to as "stem cell antibodies", for stimulating stem cell growth in vitro and in vivo. The invention also discloses methods for using the second set of antibodies, hereafter referred to as "cancer cell antibodies", for inhibiting cancer cell growth in vitro and in vivo.

In the present application, as well as in all of the applications from which the present application claims priority, names that are given to the antibodies that are disclosed in the priority applications as well as in the present application are consistent. For instance, the cancer specific antibodies MIN-C2 (also referred to herein as well as in the applications from which the present application claims priority as "C2") or MIN-E6 (also referred to herein as well as in the applications from which the present application claims priority as "E6") are the same antibodies structurally and sequence-wise as referred to in the present application as in the applications from which the present application claims priority. Likewise, the stem cell specific antibodies 2D6C3 (also referred to herein as well as in the applications from which the present application claims priority as "C3") or 2D6C8 (also referred to herein as well as in the applications from which the present application claims priority as "C8") are the same antibodies structurally and sequence-wise as referred to in the present application as in the applications from which the present application claims priority.

In a preferred embodiment, a bivalent antibody selected from the set of stem cell antibodies is administered to a patient for stimulating the growth of the patient's stem cells or progenitor cells. In a preferred embodiment, the progenitor cells are hematopoietic stem cells. In another embodiment, a bivalent antibody selected from the set of stem cell antibodies is used in vivo for stimulating the growth of a patient's stem or progenitor cells that have been mobilized using another agent, such as a CSF. In another embodiment, a bivalent antibody selected from the set of stem cell antibodies is used in vitro for stimulating the growth of a person's mobilized stem cells that have been extracted from the host for later transplantation either autologously or as donor cells transplanted into another allogeneically. In yet another embodiment, a bivalent antibody selected from the set of stem cell antibodies is used to stimulate the growth of stem cells in vivo. In another embodiment, a bivalent antibody selected from the set of stem cell antibodies is used for inducing pluripotency or inducing a less differentiated state in a set of cells. In another embodiment, antibodies selected from the set of stem cell antibodies is used to identify, select, isolate, or capture, including capture on a growth surface, stem or progenitor cells. In a preferred embodiment the stem and/or progenitor cells referred to above are human in origin. Stem cell antibodies can be used to accelerate the recovery of blood cells from effects of exposure to radiation, toxins or chemotherapy, used after bone marrow transplant, used before or after stem cell transplant which may be transplanted into the peripheral blood, and or to treat a patient who could benefit from increased production of hematopoietic stem cells or blood cells or their progenitors.

In one embodiment, antibodies selected from the set of cancer cell antibodies are used to treat cancer patients. In a preferred embodiment, antibodies selected from the set of cancer cell antibodies prevent the dimerization of the MUC1* portion of the MUC1 protein exemplified by most of the PSMGFR sequence N-terminus GTINVHDVETQF-NQYKTEAASRYNLTISDVSVSDVPFPFSAQSGA-C terminus (SEQ ID NO:1). In a more preferred embodiment, antibodies selected from the set of cancer cell antibodies, used to treat a cancer patient, are monovalent, including Fabs, single chain constructs as well as other antibodies including engineered antibody-like agents that bind to a portion of the PSMGFR sequence and prevent its ligand-induced dimerization.

MUC1* generally refers to a MUC1 protein or alternative splice isoform that is devoid of some or all of its self-aggregation domain GFLGLSNIKFRPGSVVVQLTLA-FREG (SEQ ID NO:2). In particular, MUC1* refers to MUC1 variants that lack the tandem repeat units. Most often MUC1* is a transmembrane cleavage product whose extra cellular domain consists primarily of a significant portion of the PSMGFR sequence. Because MUC1 can be cleaved at a number of positions, its exact site of cleavage may vary from one cell type to another.

In general, antibodies that belong to the group termed herein as "cancer cell antibodies" bind to the 35 amino acids that are at the C-terminal end of the PSMGFR sequence:

QFNQYKTEAASRYNLTISDVSVSDVPFPFSAQSGA (SEQ ID NO:3, also referred to in some figures as "N delta 10").

In general, antibodies that belong to the group termed herein as "stem cell antibodies" bind to the 35 amino acids that are at the N-terminal end of the PSMGFR sequence: GTINVHDVETQFNQYKTEAASRYNLTISDVSVSDV (SEQ ID NO:4, also referred to in some figures as "C delta 10") but may also bind a peptide extended N-terminally from the peptide of SEQ ID NO:4, namely including ten (10) amino acids N-terminal to SEQ ID NO:4, which are VVQLTLAFRE (SEQ ID NO:5). Alternatively, antibodies that belong to the group of stem cell antibodies are selected based on their ability to bind to the peptide of sequence VVQLTLAFREGTINVHDVETQFNQYKTEAASRYNLTISDVSVSDV (SEQ ID NO:6). In a preferred embodiment, the stem cell antibodies do not bind to the peptide SEQ ID NO:3.

Antibodies belonging to the set of cancer cell antibodies bind to a peptide containing 6-35 consecutive amino acids of the peptide of SEQ ID NO:3, which peptide may further contain up to 4 amino acid substitutions.

Antibodies belonging to the set of stem cell antibodies bind to a peptide containing 6-35 consecutive amino acids sequence of the peptide of SEQ ID NO:4, SEQ ID NO:5, or SEQ ID NO:6, which peptide may further contain up to 4 amino acid substitutions.

To generate cancer cell antibodies, the immunogenic or antigenic peptide used contains 6-35 consecutive amino acids sequence of the peptide of SEQ ID NO:3, which peptide may further contain up to 4 amino acid substitutions. In a preferred embodiment, the portions of the peptide that are more C-terminal are used to generate cancer cell antibodies. For example peptides containing amino acids ASRYNLTISDVSVSDVPFPFSAQSGA (SEQ ID NO:7) or DVSVSDVPFPFSAQSGA (SEQ ID NO:8) are used to generate cancer cell antibodies. For the generation of cancer cell antibodies of the invention, the invention also includes methods for generating humanized antibodies, selecting human antibodies, or generating antibody-like proteins in which the peptide is not used to immunize an animal but rather is used, or the nucleic acids coding for it are used, to select an antibody or antibody-like protein that recognizes at least 6 consecutive amino acids from the peptide of SEQ ID NO:3, such as the peptide of SEQ ID NO:7 or SEQ ID NO:8. Further, the peptides of SEQ ID NO:3, SEQ ID NO:7 and SEQ ID NO:8 can be used to select for antibodies that specifically modulate the growth of cancer cells but not stem cells with antibodies that bind to the more C-terminal portions such as the peptide of SEQ ID NO:7, preferred wherein SEQ ID NO:8 is especially preferred. Phage display technology may be used to select antibodies or antibody-like proteins that bind to the peptides that identify it as a cancer specific antibody. Alternatively, antibodies are generated using the entire PSMGFR peptide and cancer cell antibodies are selected based on their ability to bind to peptides that contain 6-35 consecutive amino acids sequence of the peptide of SEQ ID NO:3 or SEQ ID NO:7 or SEQ ID NO:8, which peptide may further contain up to 4 amino acid substitutions.

To generate stem cell antibodies, the immunogenic or antigenic peptide used contains 6-35 consecutive amino acids sequence of the peptide of SEQ ID NO:4 or SEQ ID NO:5 or a peptide that has sequences from both, as in SEQ ID NO:6, which peptide may further contain up to 4 amino acid substitutions. In a preferred embodiment, the portions of the peptide that are more N-terminal are used to generate stem cell antibodies. For example peptides containing amino acids VVQLTLAFREGTINVHDVETQFNQYKTEAASRYNL (SEQ ID NO:9) are preferred for the generation of stem cell antibodies. More preferred are peptides that contain consecutive amino acids from the peptide. Alternatively, antibodies are generated using the entire PSMGFR peptide and stem cell antibodies are selected based on their ability to bind to peptides that contain 6-35 consecutive amino acids sequence of the peptide of SEQ ID NO:4 or SEQ ID NO:5 or SEQ ID NO:6, which peptide may further contain up to 4 amino acid substitutions.

GTINVHDVETQFNQYKTEAASRYNL (SEQ ID NO:10) for the generation or selection of stem cell specific antibodies. Still more preferred are peptides containing consecutive amino acids from GTINVHDVETQFNQY (SEQ ID NO:11). For the generation of stem cell antibodies, the invention also includes methods for generating humanized antibodies, selecting human antibodies, or generating antibody-like proteins in which the peptide is not used to immunize an animal but rather is used, or the nucleic acids coding for it are used, to select an antibody or antibody-like protein that recognizes at least 6 consecutive amino acids from the peptide of SEQ ID NO:4, SEQ ID NO:5, SEQ ID NO:6, SEQ ID NO:9, SEQ ID NO:10, SEQ ID NO:11, wherein SEQ ID NO:10 is especially preferred. Phage display technology may be used to select antibodies or antibody-like proteins that bind to the peptides that identify it as a stem cell specific antibody.

In a preferred embodiment, antibodies belonging to the set of cancer cell antibodies will bind to MUC1-positive cancer cells as determined by ICC, FACS or other similar analysis including ELISAs and phage display in which the antibody binds to a peptide containing some or all of the amino acids of SEQ ID NO:3. In a preferred embodiment, the antibody binds to a peptide containing the last 20 amino acids at the C-terminus of SEQ ID NO:3. In a more preferred embodiment the antibody binds to a peptide containing only the last 10 amino acids at the C-terminus of the peptide of SEQ ID NO:3. In a still more preferred embodiment, antibodies belonging to the set of cancer cell antibodies bind to MUC1-positive cancer cells but not to stem or progenitor cells. In addition, antibodies belonging to the cancer cell antibody set are selected by virtue of their ability to stimulate cancer cell growth when they are bivalent and inhibit cancer cell growth when monovalent, e.g. Fab. In a yet more preferred embodiment neither the bivalent nor the monovalent form of the antibody will affect the growth of stem cells.

In a preferred embodiment, antibodies belonging to the set of stem cell antibodies bind to stem and/or progenitor cells as determined by ICC, FACS or other similar analysis including ELISAs and phage display in which the antibody binds to a peptide containing some or all of the amino acids of SEQ ID NO:4. In a preferred embodiment, the stem and/or progenitor cells are human in origin. In another preferred embodiment, the antibody binds to a peptide containing only the 20 amino acids at the N-terminus of SEQ ID NO:4. In a more preferred embodiment the antibody will bind to a peptide containing only the 10 amino acids at the N-terminus of the peptide of SEQ ID NO:4. Alternatively, the antibody will bind to the peptide of SEQ ID NO:5, SEQ ID NO:6, or a peptide containing consecutive amino acids from the combined SEQ ID NOS:4 and 5. In a still more preferred embodiment, antibodies belonging to the set of stem cell antibodies will bind to human stem and/or progenitor cells but not to MUC1-positive cancer cells. In addition, antibodies belonging to the stem cell antibody set will be selected by virtue of their ability to stimulate stem and/or progenitor cell growth when they are bivalent and inhibit stem and/or progenitor cell growth when monovalent, e.g. Fab. In a yet more preferred embodiment neither the bivalent nor the monovalent form of the antibody will affect the growth of cancer cells.

Monoclonal antibodies were generated by standard methods and antibody-producing hybridomas were selected based upon the selection criteria set out herein. Monoclonal antibodies 2D6C3 and 2D6C8 (also referred to herein as C3 and C8 respectively) were identified as stem cell antibodies. Their sequences are given in FIGS. 28 to 33. Monoclonal antibodies C2 and E6 were identified as cancer cell specific antibodies. The sequences of monoclonal antibodies C2 (MIN-C2) and E6 (MIN-E6) are given in FIGS. 24 to 27.

```
                                              (SEQ ID NO: 12)
gaggtccagctggaggagtcaggggaggcttagtgaagcctggagggtc cctgaaactctcctgtgcagcctctggattcactttcagtggctatgcca tgtcttgggttcgccagactccggagaagaggctggagtgggtcgcaacc attagtagtggtggtacttatatctactatccagacagtgtgaaggggcg attcaccatctccagagacaatgccaagaacaccctgtacctgcaaatga gcagtctgaggtctgaggacacggccatgtattactgtgcaagacttggg ggggataattactacgaatacttcgatgtctggggcgcagggaccacggt caccgtctcctccgccaaaacgacacccccatcgtctat
describes MIN-C2 Heavy chain variable region.
```

```
                                              (SEQ ID NO: 13)
EVQLEESGGGLVKPGGSLKLSCAASGFTFSGYAMSWVRQTPEKRLEWVAT

ISSGGTYIYYPDSVKGRFTISRDNAKNTLYLQMSSLRSEDTAMYYCARLG

GDNYYEYEDVWGAGTTVTVSSAKTTPPSVY
describes MIN-C2 Heavy chain variable region.
```

```
                                              (SEQ ID NO: 14)
gacattgtgatcacacagtctacagcttccttaggtgtatctctgggca gagggccaccatctcatgcagggccagcaaaagtgtcagtacatctggct atagtttatatgcactggtaccaacagagaccaggacagccacccaaactc ctcatctatcttgcatccaacctagaatctggggtccctgccaggttcag tggcagtgggtctgggacagacttcaccctcaacatccatcctgtggagg aggaggatgctgcaacctattactgtcagcacagtagggagcttccgttc acgttcggaggggggaccaagctggagataaaacgggctgatgctgcacc aactgtatcc
describes MIN-C2 Kappa chain variable region.
```

```
                                              (SEQ ID NO: 15)
DIVITQSTASLGVSLGQRATISCRASKSVSTSGYSYMHWYQQRPGQPPKL

LIYLASNLESGVPARFSGSGSGTDFTLNIHPVEEEDAATYYCQHSRELPF

TFGGGTKLEIKRADAAPTVS
describes MIN-C2 Kappa chain variable region.
```

```
                                              (SEQ ID NO: 16)
gaggttaagctggaggagtctgggggagacttagtgaagcctggagggtc cctgaaactctcctgtgcagcctctggattcactttcagtagatatggca tgtcttgggttcgccagactccagacaagaggctggagtgggtcgcaacc attagtagtggtggtacttacatctactatccagacagtgtgaaggggcg attcaccatctccagagacaatgccaagaacaccctgtacctgcaaatga
```

```
gcagtctgaagtctgaggacacagccatgtattactgtgcaagggataac tacggtagtagctacgactatgctatggactactggggtcaaggaacctc agtcaccgtctcctcagccaaaacaacagcccccatcggtctat
describes MIN-E6 Heavy chain-7 variable region.
```

```
                                              (SEQ ID NO: 17)
EVKLEESGGDLVKPGGSLKLSCAASGFTFSRYGMSWVRQTPDKRLEWVAT

ISSGGTYIYYPDSVKGRFTISRDNAKNTLYLQMSSLKSEDTAMYYCARDN

YGSSYDYAMDYWGQGTSVTVSSAKTTAPSVY
describes MIN-E6 Heavy chain-7 variable region.
```

```
                                              (SEQ ID NO: 18)
gaggtaaagctggaggagtctgggggagacttagtgaagcctggagggtc cctgaaactctcctgtgtagtctctggattcactttcagtagatatggca tgtcttgggttcgccagactccaggcaagaggctggagtgggtcgcaacc attagtggtggcggtacttacatctactatccagacagtgtgaaggggcg attcaccatctccagagacaatgccaagaacaccctgtacctgcaaatga gcagtctgaagtctgaggacacagccatgtatcactgtacaagggataac tacggtaggaactacgactacggtatggactactggggtcaaggaacctc agtcaccgtctcctcagccaaaacaacagcccccatcggtctatccactgg cccctgtgtgtggagatacaactggctcctcggtgactctaggatgcctg gtcaag
describes MIN-E6 Heavy chain-8 variable region.
```

```
                                              (SEQ ID NO: 19)
EVKLEESGGDLVKPGGSLKLSCVVSGFTFSRYGMSWVRQTPGKRLEWVAT

ISGGGTYIYYPDSVKGRFTISRDNAKNTLYLQMSSLKSEDTAMYHCTRDN

YGRNYDYGMDYWGQGTSVTVSSAKTTAPSVYPLAPVCGDTTGSSVTLGCL

VK
describes MIN-E6 Heavy chain-8 variable region.
```

```
                                              (SEQ ID NO: 20)
gatattgtgatcacccagactacagcaatcatgtctgcatctccaggggga ggaggtcaccctaacctgcagtgccacctcaagtgtaagttacatacact ggttccagcagaggccaggcacttctcccaaactctggatttatagcaca tccaacctggcttctggagtccctgttcgcttcagtggcagtggatatgg gacctcttactctctcacaatcagccgaatggaggctgaagatgctgcca cttattactgccagcaaaggagtagttccccattcacgttcggctcgggg acaaagttggaaataaaacgggctgatgctgcaccaactgtatcc
describes MIN-E6 Kappa chain variable region.
```

```
                                              (SEQ ID NO: 21)
DIVITQTTAIMSASPGEEVTLTCSATSSVSYIHWFQQRPGTSPKLWIYST

SNLASGVPVRFSGSGYGTSYSLTISRMEAEDAATYYCQQRSSSPFTFGSG

TKLEIKRADAAPTVS
describes MIN-E6 Kappa chain variable region.
```

```
                                              (SEQ ID NO: 22)
gaggtccagctggaggagtctgggggaggcttagtgaagcctggagggtc cctgaaactctcctgtgcagcctctggattcactttcagtggctatgcca tgtcttgggttcgccagactccggagaagaggctggagtgggtcgcaacc attagtagtggtggtacttatatctactatccagacagtgtgaaggggcg
```

-continued

```
attcaccatctccagagacaatgccaagaacaccctgtacctgcaaatga gcagtctgaggtctgaggacacggccatgtattactgtgcaagacttggg ggggataattactacgaatacttcgatgtctggggcgcagggaccacggt caccgtctcctccgccaaaacgacaccccatctgtctatccactggccc ctggatctgctgcccaaactaactccatggtgaccctgggatgcctggtc aagggctatttccctgagccagtgacagtgacctggaactctggatccct gtccagcggtgtgcacaccttcccagctgtcctgcagtctgacctctaca ctctgagcagctcagtgactgtcccctccagcacctggcccagcgagacc gtcacctgcaacgttgcccacccagccagcaggaccgcg
describes MIN-C2 Fab Heavy chain.
```

(SEQ ID NO: 23)
```
gacattgtgatcacacagtctacagcttccttaggtgtatctctgggca gagggccaccatctcatgcagggccagcaaaagtgtcagtacatctggct atagttatatgcactggtaccaacagagaccaggacagccacccaaactc ctcatctatcttgcatccaacctagaatctggggtccctgccaggttcag tggcagtgggtctgggacagacttcaccctcaacatccatcctgtggagg aggaggatgctgcaacctattactgtcagcacagtagggagcttccgttc acgttcggaggggggaccaagctggagataaaacgggctgatgctgcacc aactgtatccatcttcccaccatccagtgagcagttaacatctggaggtg cctcagtcgtgtgcttcttgaacaacttctacccaaagacatcaatgtc aagtggaagattgatggcagtgaacgacaaaatggcgtcctgaacagttg gactgatcaggacagcaaagacagcacctacagcatgagcagcaccctca cgttgaccaaggacgagtatgaacgacataacagctatacctgtgaggcc actcacaagacatcaacttcacccattgtcaagagcttcaacaggaatga gtgt
describes MIN-C2 Fab Kappa chain.
```

(SEQ ID NO: 24)
EVQLEESGGGLVKPGGSLKLSCAASGFTFSGYAMSWVRQTPEKRLEWVAT
ISSGGTYIYYPDSVKGRFTISRDNAKNTLYLQMSSLRSEDTAMYYCARLG
GDNYYEYFDVWGAGTTVTVSSAKTTPPSVYPLAPGSAAQTNSMVTLGCLV
KGYFPEPVTVTWNSGSLSSGVHTFPAVLQSDLYTLSSSVTVPSSTWPSET
VTCNVAHPASRTA
describes MIN-C2 Fab Heavy chain.

(SEQ ID NO: 25)
DIVITQSTASLGVSLGQRATISCRASKSVSTSGYSYMHWYQQRPGQPPKL
LIYLASNLESGVPARFSGSGSGTDFTLNIHPVEEEDAATYYCQHSRELPF
TFGGGTKLEIKRADAAPTVSIFPPSSEQLTSGGASVVCFLNNFYPKDINV
KWKIDGSERQNGVLNSWTDQDSKDSTYSMSSTLTLTKDEYERHNSYTCEA
THKTSTSPIVKSFNRNEC
describes MIN-C2 Fab Kappa chain.

(SEQ ID NO: 26)
RADAAPTVSIFPPSSEQLTSGGASVVCFLNNFYPKDINVKWKIDGSERQN
GVLNSWTDQDSKDSTYSMSSTLTLTKDEYERHNSYTCEATHKTSTSPIVK
SFNRNEC
describes MIN-C2 light CL region amino acid sequence.

(SEQ ID NO: 27)
FDVWGAGTTVTVSSAKTTPPSVYPLAPGSAAQTNSMVTLGCLVKGYFPEP
VTVTWNSGSLSSGVHTFPAVLQSDLYTLSSSVTVPSSTWPSETVTCNVAH
PASRTA
describes MIN-C2 heavy chain CH1 region amino acid sequence.

(SEQ ID NO: 28)
DIVITQSTASLGVSLGQRATISC
describes MIN-C2 light chain variable framework region 1 (FWR1) amino acid sequence.

(SEQ ID NO: 29)
DIVITQTTAIMSASPGEEVTLTC
describes MIN-E6 light chain variable framework region 1 (FWR1) amino acid sequence.

(SEQ ID NO: 30)
RASKSVSTSGYSYMH
describes MIN-C2 light chain variable complementarity determining region 1 (CDR1) amino acid sequence.

(SEQ ID NO: 31)
SATSSVSYIH
describes MIN-E6 light chain variable complementarity determining region 1 (CDR1) amino acid sequence.

(SEQ ID NO: 32)
WYQQRPGQPPKLLIY
describes MIN-C2 light chain variable framework region 2 (FWR2) amino acid sequence.

(SEQ ID NO: 33)
WFQQRPGTSPKLWIY
describes MIN-E6 light chain variable framework region 2 (FWR2) amino acid sequence.

(SEQ ID NO: 34)
LASNLES
describes MIN-C2 light chain variable complementarity determining region 2 (CDR2) amino acid sequence.

(SEQ ID NO: 35)
STSNLAS
describes MIN-E6 light chain variable complementarity determining region 2 (CDR2) amino acid sequence.

(SEQ ID NO: 36)
GVPARFSGSGSGTDFTLNIHPVEEEDAATYYC
describes MIN-C2 light chain variable framework region 3 (FWR3) amino acid sequence.

(SEQ ID NO: 37)
GVPVRFSGSGYGTSYSLTISRMEAEDAATYYC
describes MIN-E6 light chain variable framework region 3 (FWR3) amino acid sequence.

(SEQ ID NO: 38)
QHSRELPFT
describes MIN-C2 light chain variable complementarity determining region 3 (CDR3) amino acid sequence.

(SEQ ID NO: 39)
QQRSSSPFT
describes MIN-E6 light chain variable complementarity determining region 3 (CDR3) amino acid sequence.

(SEQ ID NO: 40)
EVQLEESGGGLVKPGGSLKLSCAASGFTFS
describes MIN-C2 heavy chain variable framework region 1 (FWR1) amino acid sequence.

-continued (SEQ ID NO: 41)
EVKLEESGGDLVKPGGSLKLSCAASGFTFS
describes MIN-E6-7 heavy chain variable
framework region 1 (FWR1) amino acid sequence.

(SEQ ID NO: 42)
EVKLEESGGDLVKPGGSLKLSCVVSGFTFS
describes MIN-E6-8 heavy chain variable
framework region 1 (FWR1) amino acid sequence.

(SEQ ID NO: 43)
GYAMS
describes MIN-C2 heavy chain variable
complementarity determining region 1 (CDR1)
amino acid sequence.

(SEQ ID NO: 44)
RYGMS
describes MIN-E6-7 heavy chain variable
complementarity determining region 1 (CDR1)
amino acid sequence.

(SEQ ID NO: 45)
RYGMS
describes MIN-E6-8 heavy chain variable
complementarity determining region 1 (CDR1)
amino acid sequence.

(SEQ ID NO: 46)
WVRQTPEKRLEWVA
describes MIN-C2 heavy chain variable
framework region 2 (FWR2) amino acid sequence.

(SEQ ID NO: 47)
WVRQTPDKRLEWVA
describes MIN-E6-7 heavy chain variable
framework region 2 (FWR2) amino acid sequence.

(SEQ ID NO: 48)
WVRQTPGKRLEWVA
describes MIN-E6-8 heavy chain variable
framework region 2 (FWR2) amino acid sequence.

(SEQ ID NO: 49)
TISSGGTYIYYPDSVKG
describes MIN-C2 heavy chain variable
complementarity determining region 2 (CDR2)
amino acid sequence.

(SEQ ID NO: 50)
TISSGGTYIYYPDSVKG
describes MIN-E6-7 heavy chain
variable complementarity determining region 2
(CDR2) amino acid sequence.

(SEQ ID NO: 51)
TISGGGTYIYYPDSVKG
describes MIN-E6-8 heavy chain
variable complementarity determining region 2
(CDR2) amino acid sequence.

(SEQ ID NO: 52)
RFTISRDNAKNTLYLQMSSLRSEDTAMYYCAR
describes MIN-C2 heavy chain variable framework
region 3 (FWR3) amino acid sequence.

(SEQ ID NO: 53)
RFTISRDNAKNTLYLQMSSLKSEDTAMYYCAR
describes MIN-E6-7 heavy chain variable framework
region 3 (FWR3) amino acid sequence.

(SEQ ID NO: 54)
RFTISRDNAKNTLYLQMSSLKSEDTAMYHCTR
describes MIN-E6-8 heavy chain variable framework
region 3 (FWR3) amino acid sequence.

(SEQ ID NO: 55)
LGGDNYYEY
describes MIN-C2 heavy chain variable
complementarity determining region 3
(CDR3) amino acid sequence.

(SEQ ID NO: 56)
DNYGSSYDYA
describes MIN-E6-7 heavy chain variable
complementarity determining region 3
(CDR3) amino acid sequence.

(SEQ ID NO: 57)
DNYGRNYDYG
describes MIN-E6-8 heavy chain variable
complementarity determining region 3 (CDR3)
amino acid sequence.

(SEQ ID NO: 58)
EVQLVESGGGLVKPGGSLRLSCA ASGFTFS
describes IGHV3 (name from Igblast): FWR1: Human
IgG antibody framework region sequence with 84.7%
homology (249/294) to variable heavy chain region
of MIN-C2.

(SEQ ID NO: 59)
WVRQAPGKGLEWVS
describes IGHV3 (name from Igblast):
FWR2: Human IgG antibody framework region
sequence with 84.7% homology (249/294) to
variable heavy chain region of MIN-C2.

(SEQ ID NO: 60)
RFTISRDNAKNSLYLQMNSLRAEDTAV
describes IGHV3 (name from Igblast): FWR3:
Human IgG antibody framework region sequence with
84.7% homology (249/294) to variable heavy chain
region of MIN-C2.

(SEQ ID NO: 61)
DIVLTQSPASLAVSPGQRATITC
describes IGkV7 (name from Igblast): FWR1: Human
IgG antibody framework region sequence with 76.4%
homology (226/296) to variable light chain region
of MIN-C2.

(SEQ ID NO: 62)
WYQQKPGQPPKLLIY
describes IGkV7 (name from Igblast): FWR2: Human
IgG antibody framework region sequence with
76.4% homology (226/296) to variable light chain
region of MIN-C2.

(SEQ ID NO: 63)
GVPARFSGSGSGTDFTLTINPVEANDTANYY
describes IGkV7 (name from Igblast): FWR 3: Human
IgG antibody framework region sequence with 76.4%
homology (226/296) to variable light chain region
of MIN-C2.

(SEQ ID NO: 64)
EVQLVESGGGLVKPGGSLRLSCAASGFTFS
describes IGHV3 (name from Igblast): FWR1:
Human IgG antibody framework region sequence with
84.1% homology (249/296) to variable heavy chain
region of MIN-E6.

(SEQ ID NO: 65)
WVRQAPGKGLEWVS
describes IGHV3 (name from Igblast): FWR2: Human
IgG antibody framework region sequence with
84.1% homology (249/296) to variable heavy
chain region of MIN-E6.

(SEQ ID NO: 66)
RFTISRDNAKNSLYLQMNSLRAEDTAVYYCAR
describes IGHV3 (name from Igblast): FWR3:
Human IgG antibody framework region sequence with
84.1% homology (249/296) to variable heavy chain
region of MIN-E6.

```
                                                          (SEQ ID NO: 67)
EIVMTQSPATLSVSPGERATLSC
describes IGkV3 (name from Igblast): FWR1: Human
IgG antibody framework region sequence with 69.5%
homology (187/269) to variable light chain region
of MIN-E6.
                                                          (SEQ ID NO: 68)
WFQQRPGTSPK LLIY
describes IGkV3 (name from Igblast):
FWR2: Human IgG antibody framework region sequence
with 69.5% homology (187/269) to variable light
chain region of MIN-E6.

(SEQ ID NO: 69)
GIPARFSGSGSGTEFTLTISSLQSEDFAVYYC
describes IGkV3 (name from Igblast): FWR3: Human
IgG antibody framework region sequence with 69.5%
homology (187/269) to variable light chain region
of MIN-E6.
```

Figure 2:
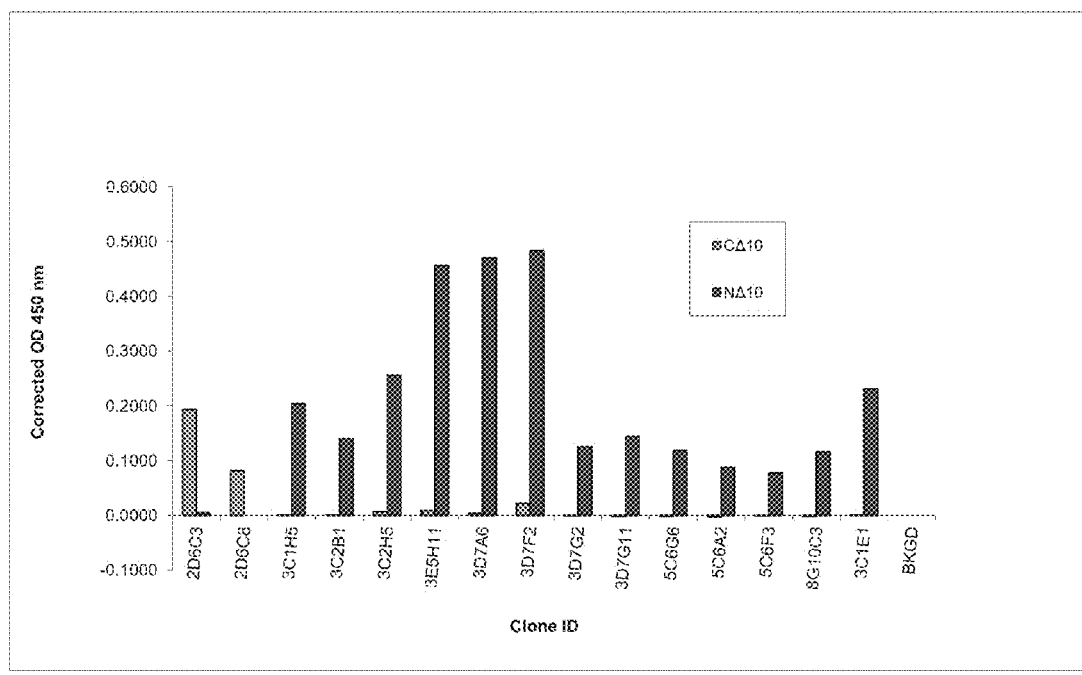
FIG. 2 is a graph from an ELISA experiment showing binding of various antibody clones to either a PSMGFR peptide lacking the N-terminal 10 amino acids (N delta 10: SEQ ID NO:3) or a PSMGFR peptide lacking the C-terminal 10 amino acids (C delta 10: SEQ ID NO:4).
Figure 3:
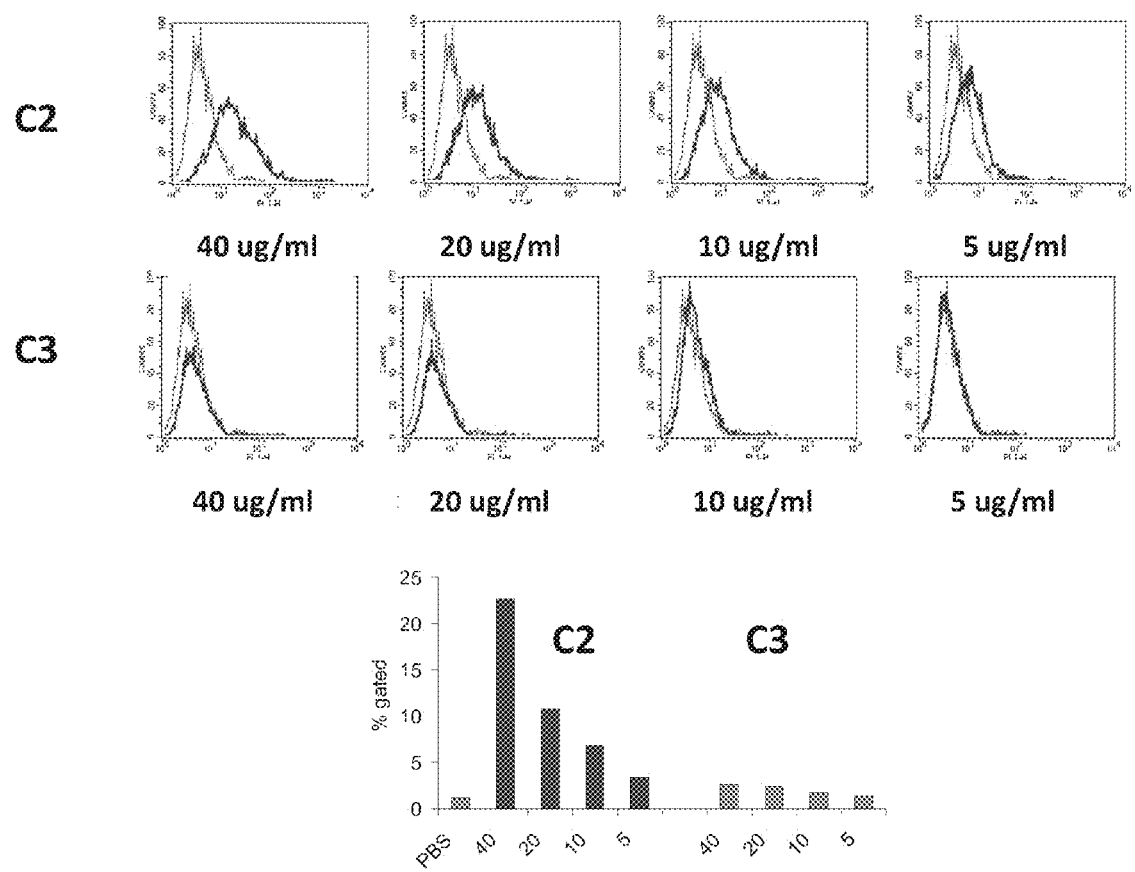
FIG. 3 shows FACS showing the response of MUC1-positive T47D breast cancer cells to either cancer cell specific antibody C2 (MIN-C2) or stem cell specific antibody C3 (2D6C3) plus the data presented graphically.
Figure 4:
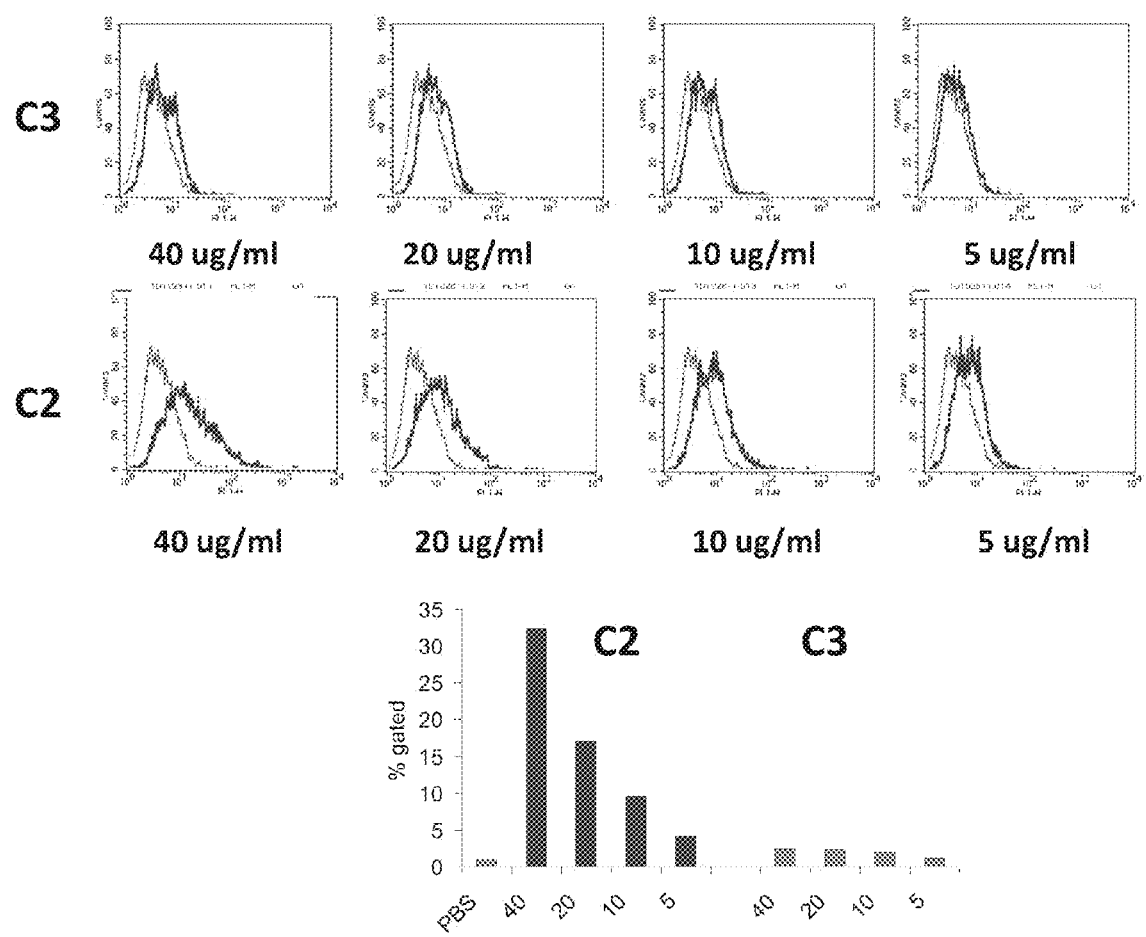
FIG. 4 shows FACS showing the response of MUC1-positive ZR-75-1 breast cancer cells to either cancer specific antibody C2 (MIN-C2) or stem cell specific antibody C3 (2D6C3) plus the data presented graphically.
Figure 5:
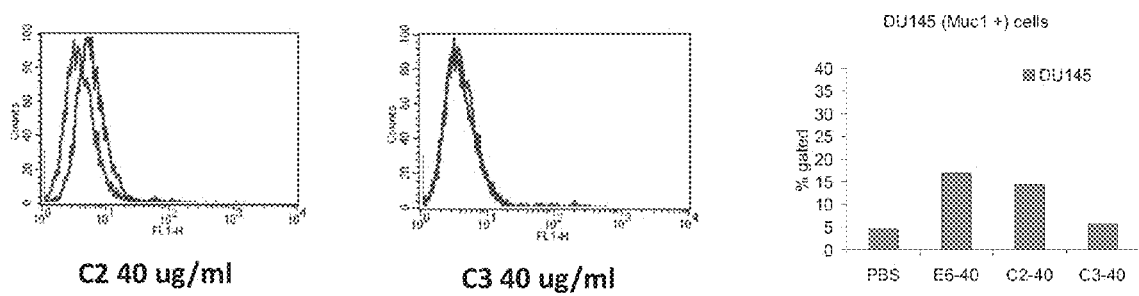
FIG. 5 shows FACS showing the response of MUC1-positive DU145 prostate cancer cells to either cancer specific antibody C2 (MIN-C2) or stem cell specific antibody C3 (2D6C3) plus the data presented graphically.
Figure 6:
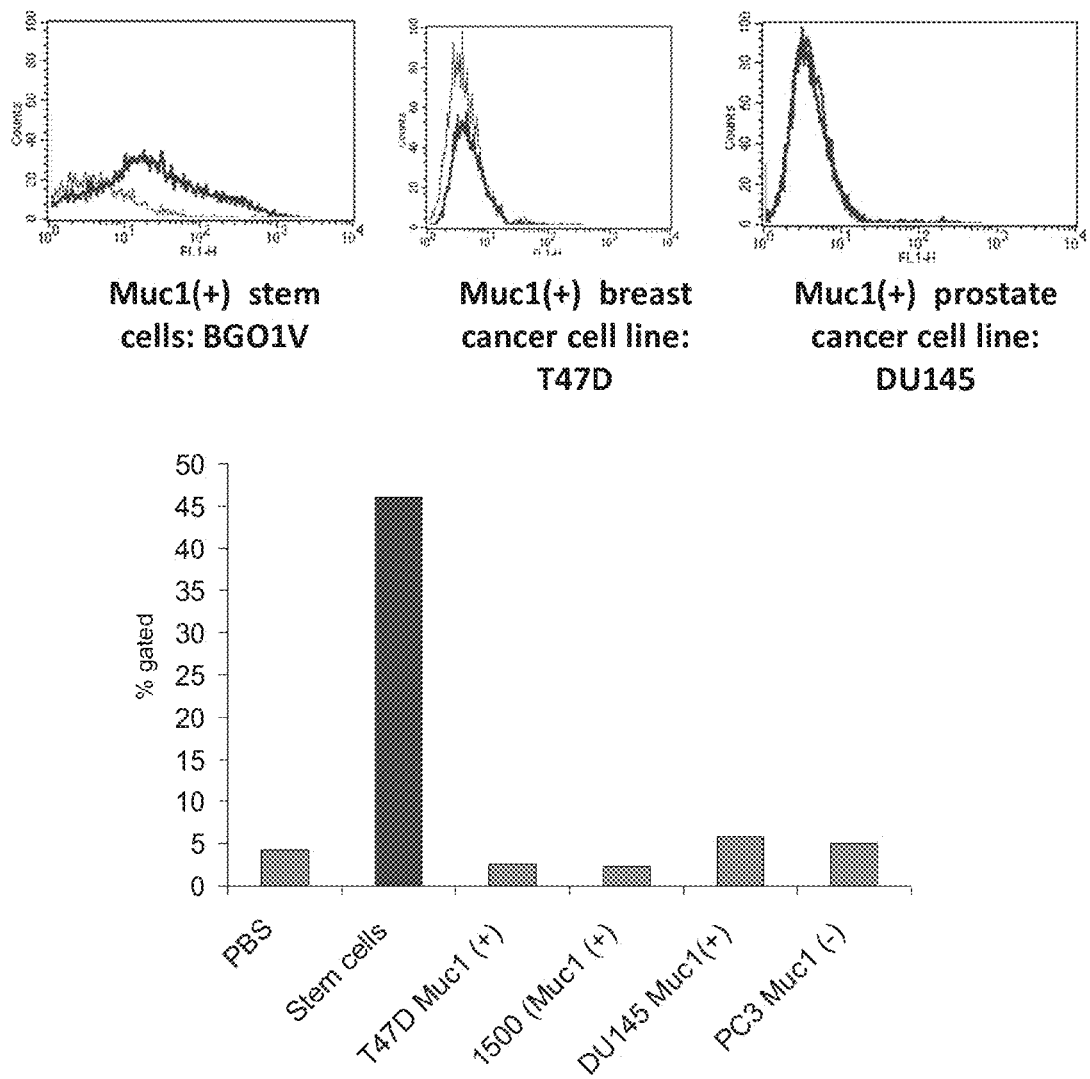
FIG. 6 shows FACS showing the response of either MUC1-positive embryonic BGO1V/hOG human stem cells, MUC1-positive T47D breast cancer cells, or MUC1-positive DU145 prostate cancer cells to stem cell specific antibody C3 (2D6C3) plus the data presented graphically.

Antibodies produced by the various clones were tested first by ELISA. Ideally, cancer cell specific antibodies would bind to the peptide SEQ ID NO:3 lacking the last 10 N-terminal amino acids of the PSMGFR peptide (SEQ ID NO:1), but not to the peptide of SEQ ID NO:4, lacking the last 10 amino acids at the C-terminus of the PSMGFR peptide. Ideally, the stem cell specific antibodies would have the opposite binding pattern; they should bind to peptide of SEQ ID NO:4 but not to peptide of SEQ ID NO:3. By ELISA, monoclonal antibodies 2D6C3 and 2D6C8 (also referred to herein as C3 and C8 respectively) bound to the peptide of SEQ ID NO:4 but not to the peptide of SEQ ID NO:3. Conversely, monoclonal antibodies C2 and E6 bound to the peptide of SEQ ID NO:3 but not to the peptide of SEQ ID NO:4, see FIG. 2.

In another method to identify monoclonal antibodies that were specific for stem cells, antibodies were coated onto the surface of a cell culture plate. Because human stem cells are not adherent, they should not attach to the plate unless the plate is coated with an antibody that recognizes a receptor on the surface of the stem cells. In this way, clones 2D6C3 and 2D6C8 (also referred to herein as C3 and C8 respectively) were identified as being stem cell specific antibodies. In a preferred embodiment, the antibodies bound to a peptide whose sequence corresponds to the MUC1* extra cellular domain but not to the membrane proximal portion (SEQ ID NO:3). In a more preferred embodiment, the antibodies bound to the distal portion peptide (SEQ ID NO:4, SEQ ID NO:5, SEQ ID NO:6) of the PSMGFR peptide and not to the membrane proximal portion (SEQ ID NO:3), The monoclonal antibodies can additionally be tested for binding specificity by FACS to determine if they bound to cancer cells or stem cells. FIGS. 3-6 show FACS data that collectively show that the cancer specific antibodies C2 (MIN-C2) and E6 (MIN-E6) only bind to MUC1-positive cancer cells but not to human stem cells. Conversely, FIGS. 3-6 show that stem cell antibodies 2D6C3 and 2D6C8 only bind to stem cells and not to cancer cells.

Figure 7:
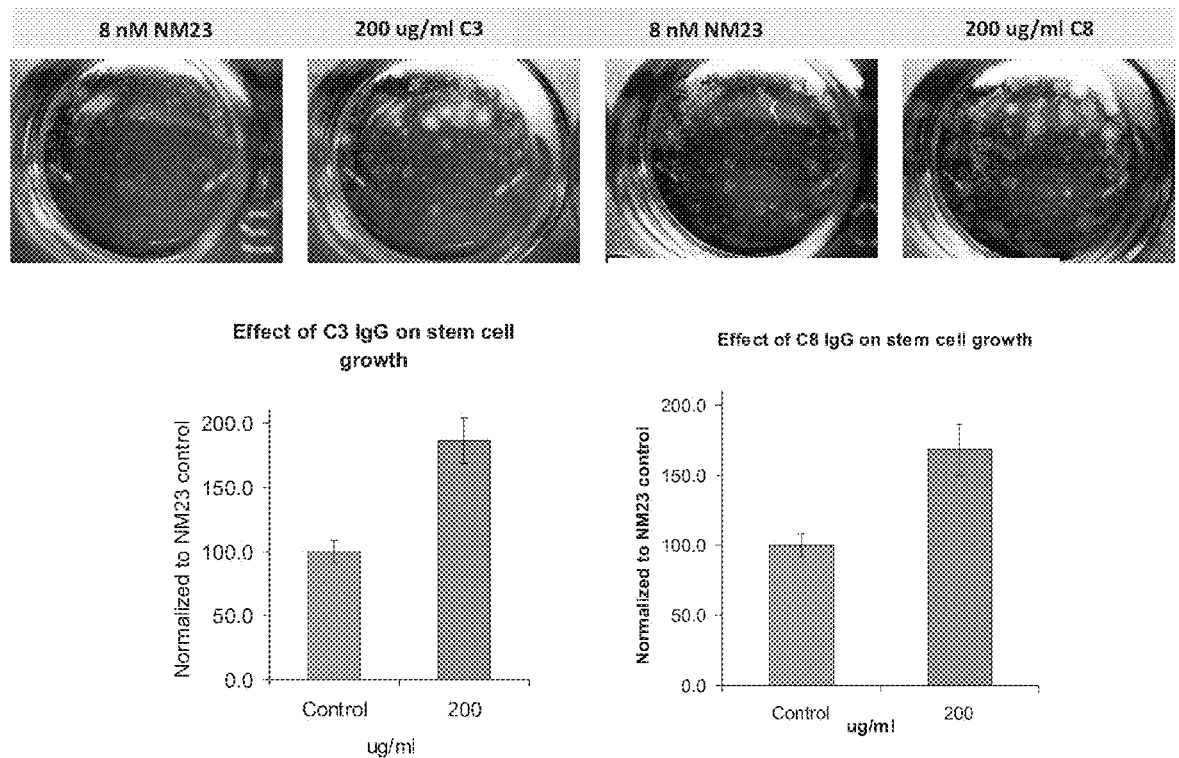
FIG. 7 shows photographs of BGO1V/hOG embryonic stem cells growing in plates in the presence of either the control 8 nM NM23 (dimeric), 200 ug/ml bivalent C3 (2D6C3) stem cell specific monoclonal antibody, or 200 ug/ml bivalent C8 (2D6C8) stem cell specific monoclonal antibody. Resultant cells were measured after 72 hour growth period and measured in a Vialight assay and graphed as shown.
Figure 8:
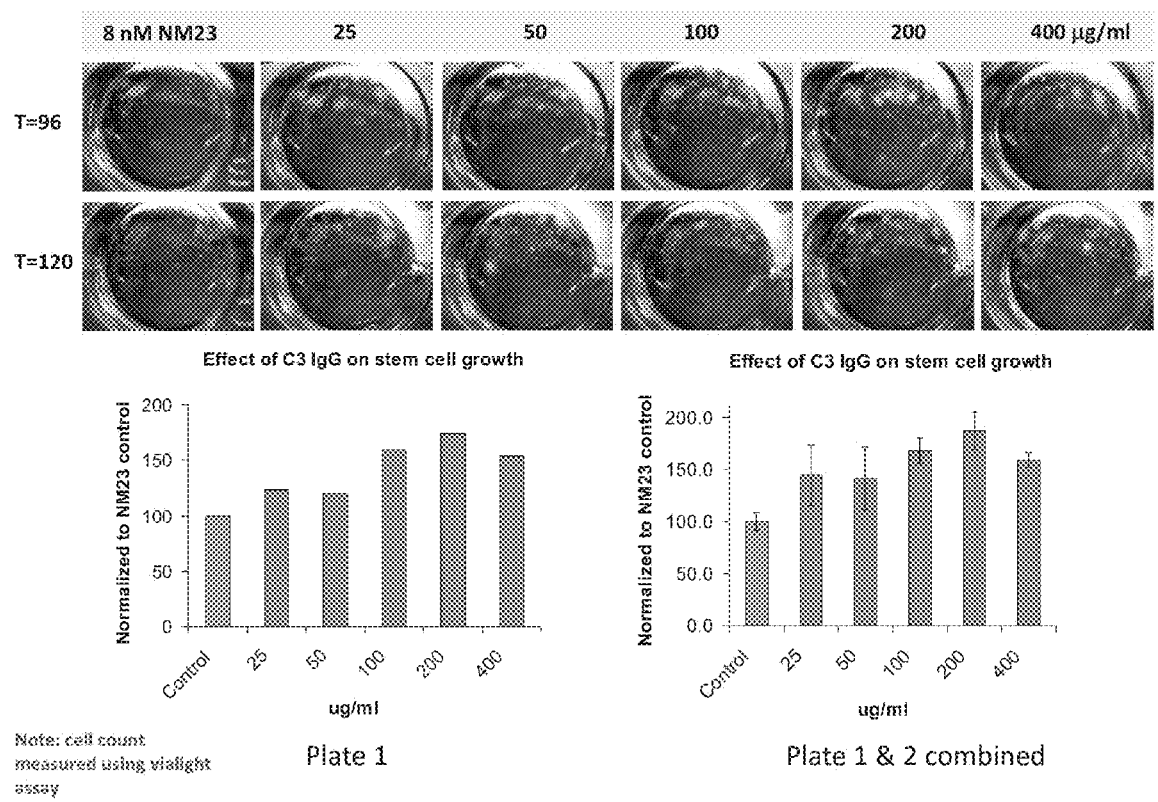
FIG. 8 shows photographs of BGO1V/hOG embryonic stem cells growing in plates in the presence of either the control 8 nM NM23 (dimeric) or bivalent C3 (2D6C3) stem cell specific monoclonal antibody at the concentrations shown. Resultant cells were measured after 72 hour growth period and measured in a Vialight assay and graphed as shown. Cell count was measured using vialight assay.
Figure 9:
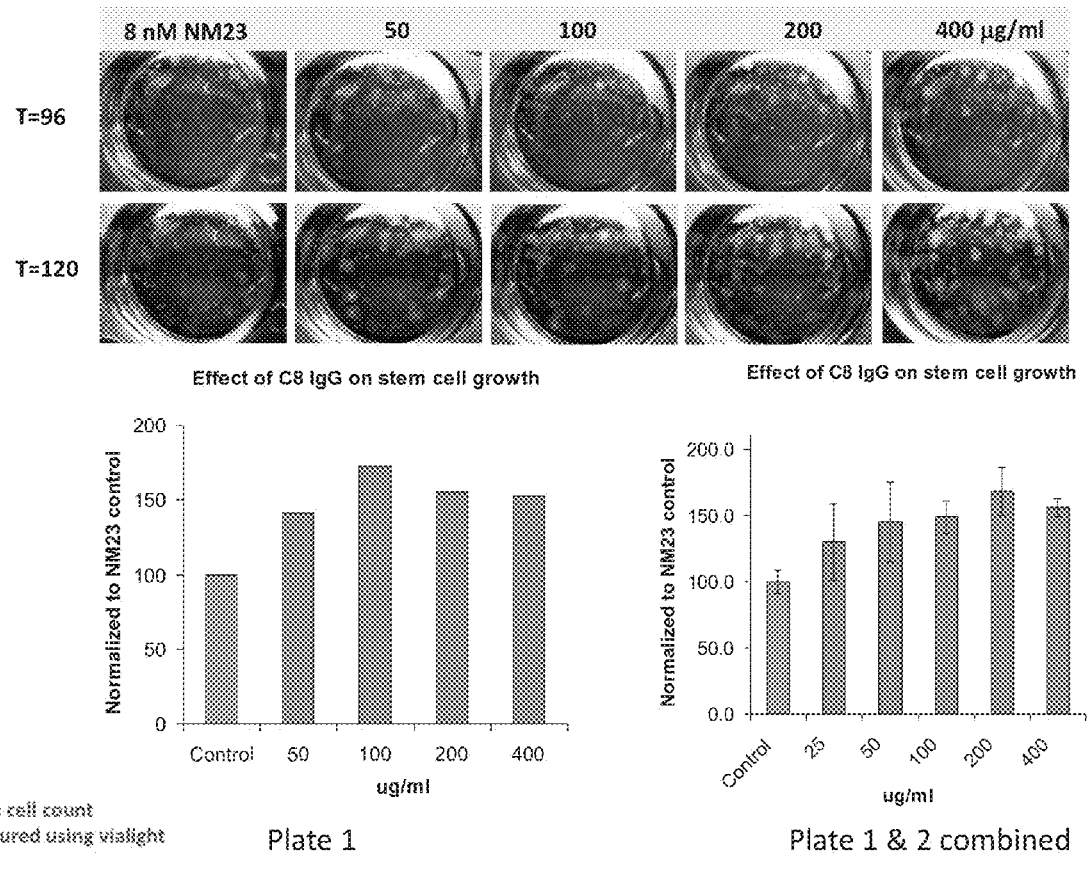
FIG. 9 shows photographs of BGO1V/hOG embryonic stem cells growing in plates in the presence of either the control 8 nM NM23 (dimeric) or bivalent C8 (2D6C8) stem cell specific monoclonal antibody at the concentrations shown. Resultant cells were measured after 72 hour growth period and measured in a Vialight assay and graphed as shown. Cell count was measured using vialight assay.
Figure 12:
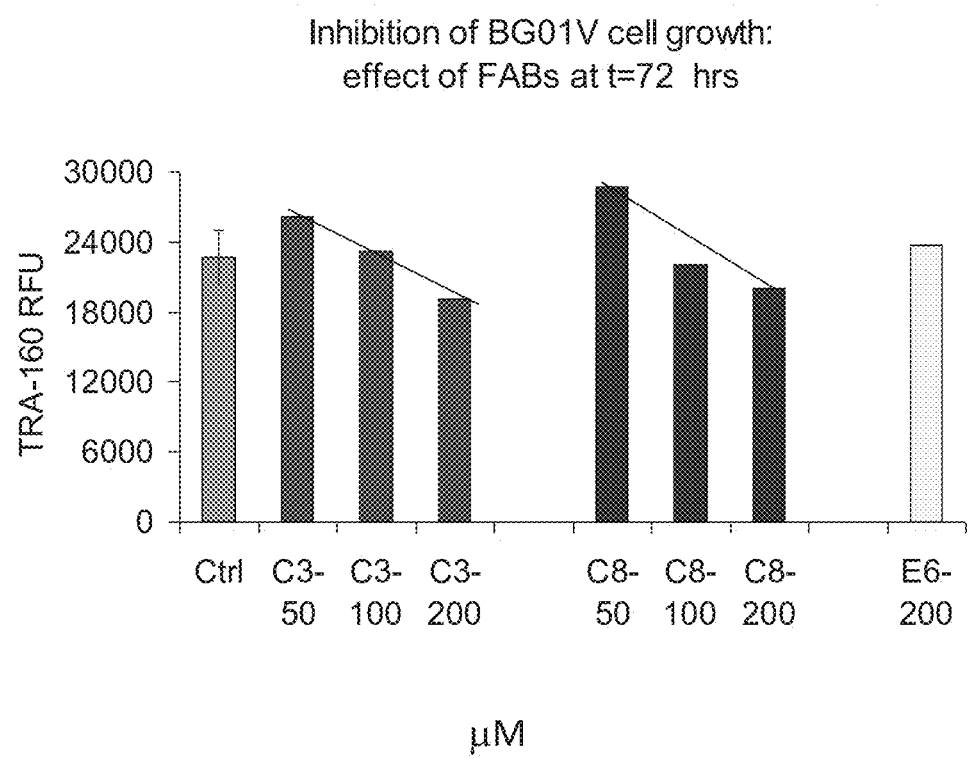
FIG. 12 shows a graph of measured Tra 1-60, a marker on undifferentiated stem cells, after stem cells were treated with either the control (Ctrl) 8 nM NM23 (dimeric) or the Fab of either stem cell specific monoclonal antibodies C3 (2D6C3) and C8 (2D6C8) or with the Fab of cancer specific monoclonal antibody E6 (MIN-E6). Results show that by another measure, the cancer specific antibody did not inhibit the growth of stem cells.
Figure 13:
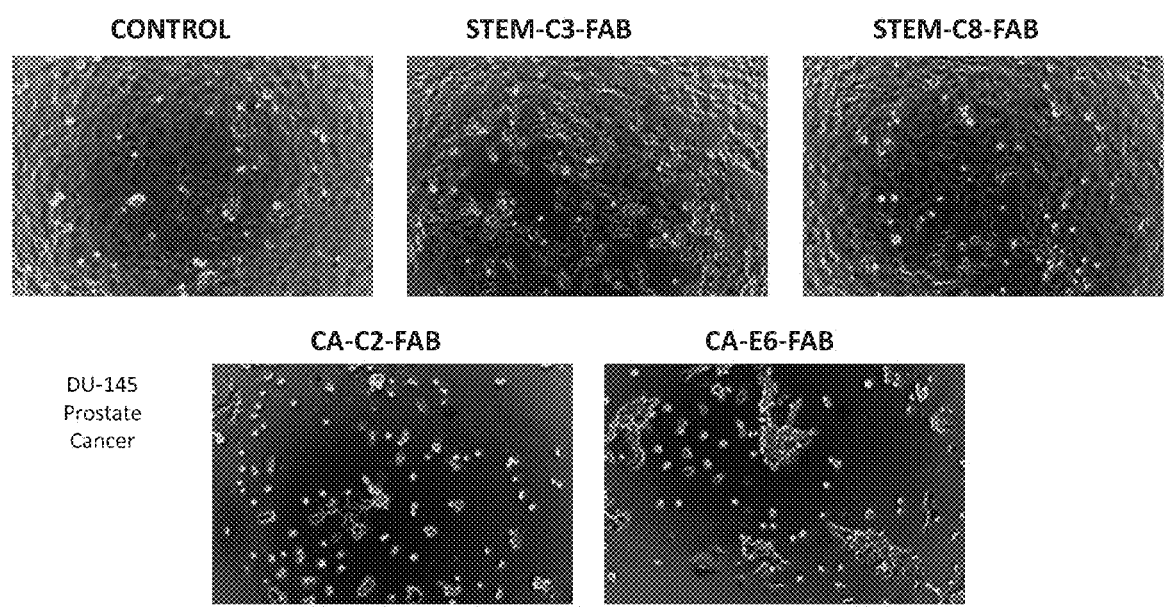
FIG. 13 shows photographs of MUC1-positive DU145 prostate cancer cells after treatment with either the Fab of cancer specific antibody C2 (CA-C2-Fab (MIN-C2)), Fab of E6 (CA-E6-Fab (MIN-E6)) or the Fabs of stem cell specific antibodies C3 (STEM-C3-Fab (2D6C3)) or C8 (STEM-C8-Fab (2D6C8)), showing that only the Fabs of the cancer specific antibodies inhibited the growth of cancer cells.
Figure 16:
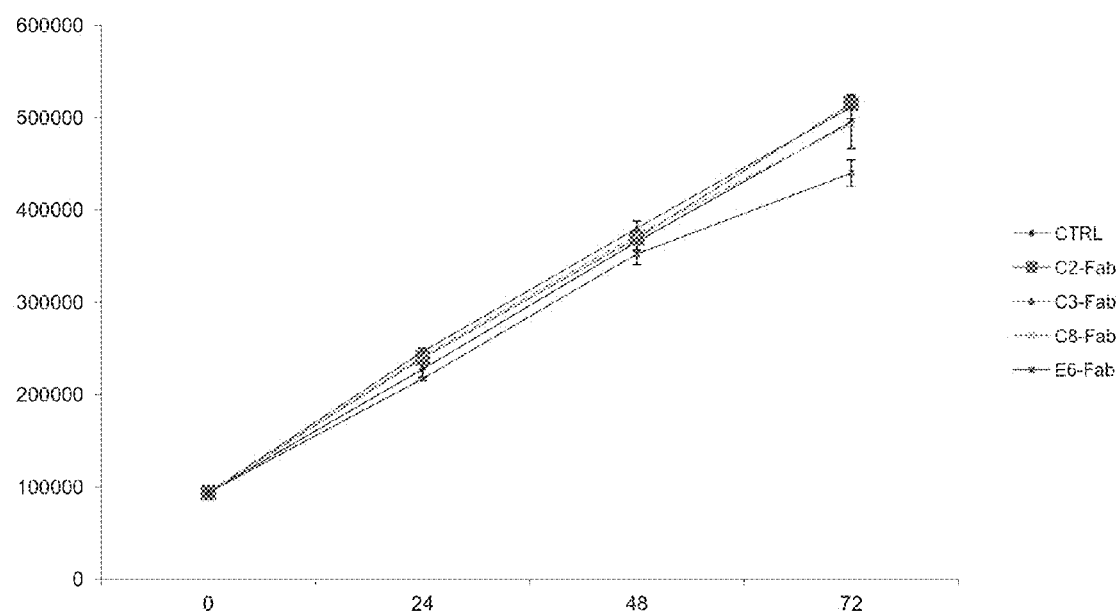
FIG. 16 is a graph of cell counts of MUC1-negative PC3 prostate cancer cells, which are MUC1 negative, after treatment with either the Fab of cancer specific antibody C2 (C2-Fab (MIN-C2)), Fab of E6 (E6-Fab (MIN-E6)) or the Fabs of stem cell specific antibodies C3 (C3-Fab (2D6C3)) or C8 (C8-Fab (2D6C8)), showing that none of the Fabs had any effect on MUC1-negative cancer cells.

As yet another test to determine the specificity of monoclonal antibodies, their effect on the growth of either stem cells or cancer cells can be tested. As can be seen in the cartoon of FIG. 1, bivalent anti-MUC1* antibodies dimerize the extra cellular domain of MUC1* and stimulate growth, while the monovalent Fabs inhibit growth. The bivalent forms of the antibodies were tested for their ability to stimulate the growth of human stem cells and the monovalent Fabs were tested for their ability to inhibit the growth of the stem cells. FIGS. 7-9 show photographs and plotted data showing that bivalent stem cell antibodies 2D6C3 and 2D6C8 (C3 and C8) stimulate human stem cell growth. FIGS. 10-12 show that the Fab of the stem cell antibody C3 at 100 uM inhibits growth of stem cells but the Fabs of the cancer specific antibodies C2 (MIN-C2) and E6 (MIN-E6) do not. FIGS. 13-15 show that the Fabs of the cancer specific antibodies C2 (MIN-C2) and E6 (MIN-E6) inhibit the growth of MUC1-positive cancer cells but the Fabs of the stem cell specific antibodies 2D6C3 and 2D6C8 (C3 and C8) do not. FIG. 16 shows that none of the Fabs of the cancer specific or stem specific antibodies have any effect on MUC1-negative cells, such as PC3 prostate cancer cells.

Figure 17:
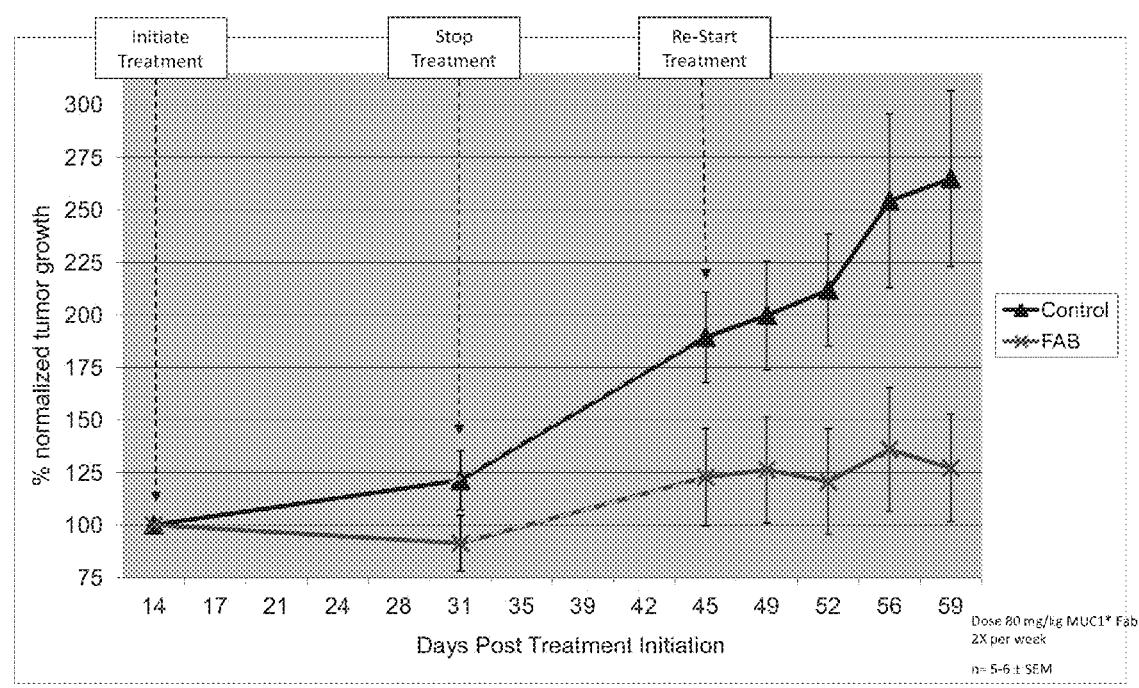
FIG. 17 is the graphical representation of the results of an experiment in which nude mice were xenografted with human T47D breast tumors then treated with either vehicle (control) or 80 mg/kg E6 (MIN-E6) Fab 2-times per week. Treatment commenced at Day 14 post implantation, then was suspended for 15 days, then resumed.
Figure 18:
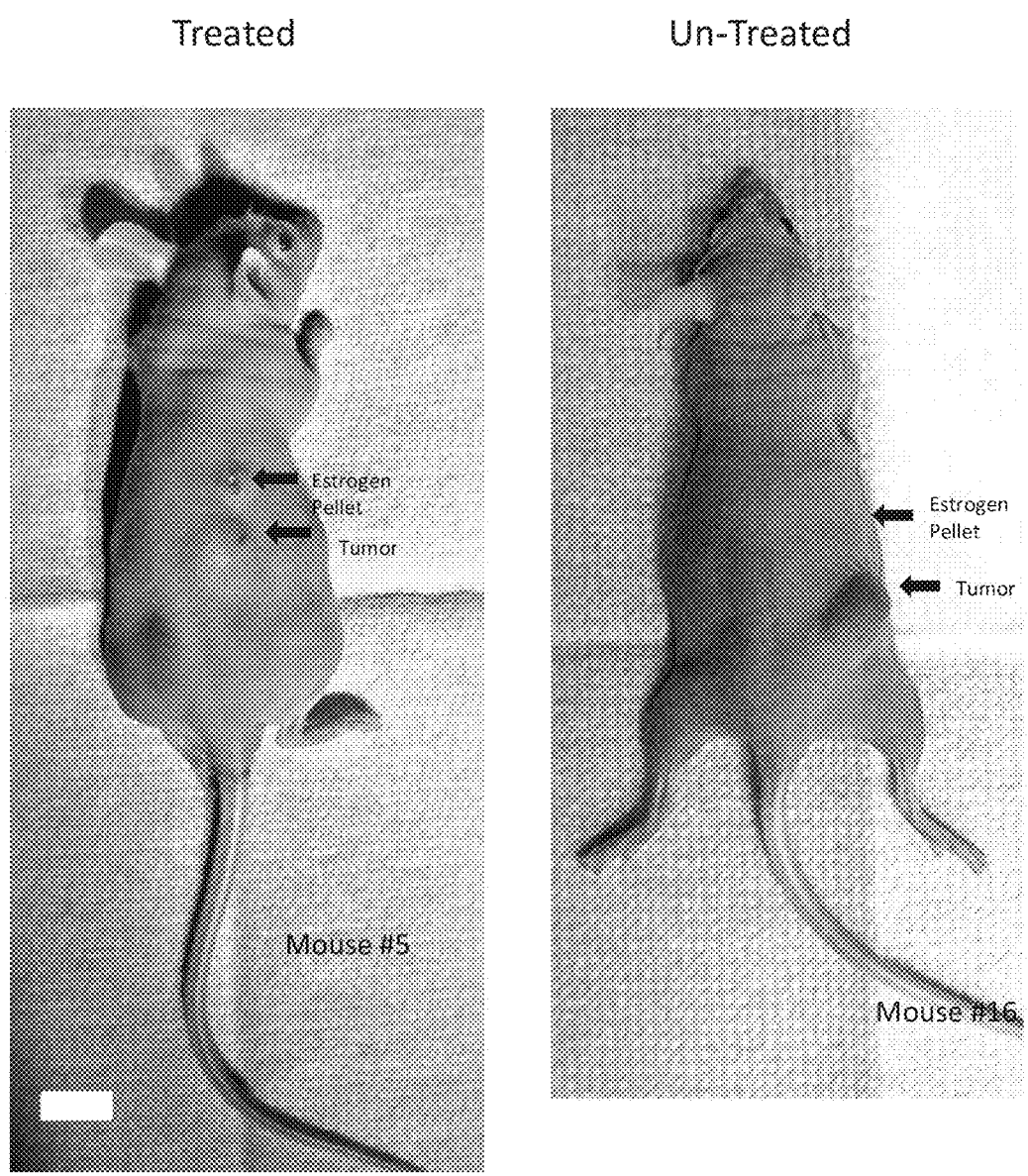
FIG. 18 shows that anti-MUC1* Fab shrinks tumors and reduces expression of MUC1* growth factor receptor.

As yet a further test of binding specificity, antibodies selected to be stem specific can be tested in vivo and assayed for their ability to stimulate stem or progenitor cell growth. Cancer specific antibodies can be tested in vivo for their ability to inhibit cancer cell growth. In one example, to test the in vivo effects of a cancer cell antibody identified using methods of the invention, female nude mice, into which estrogen pellets had been implanted, were xenografted with human breast tumor cells (T47D). Tumors were allowed to engraft for 14 days before the mice were treated with 80 mg/kg of the E6 Fab 2-times per week. An equal number of control mice were injected with buffer alone. Treatment was suspended during the 14 day period between Day 31 and Day 45 to determine whether the treated mice would develop a resistance to the treatment. The graph of FIG. 17 shows that the E6 Fab effectively reduced tumor growth rate and volume compared to the control mice. The fact that after a 14 day lapse of treatment, the mice continued to respond to the E6 Fab shows that they did not develop a resistance to the drug. FIG. 18 shows photographs of two of the mice from the study.

Figure 19:
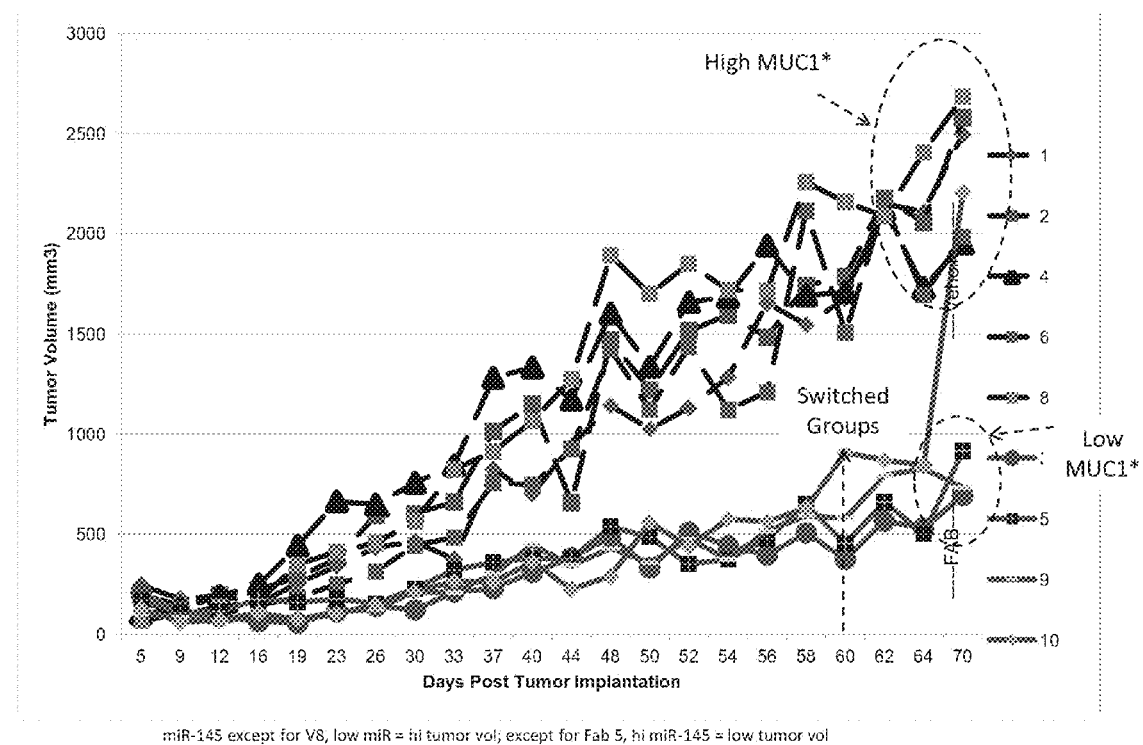
FIG. 19 shows a graph of tumor volume for NOD/SCID mice xenografted with human prostate tumor line DU145, wherein half the mice were treated with E6 Fab at 160 mg/kg every 48 hours and the other half treated with vehicle alone.
Figure 20:
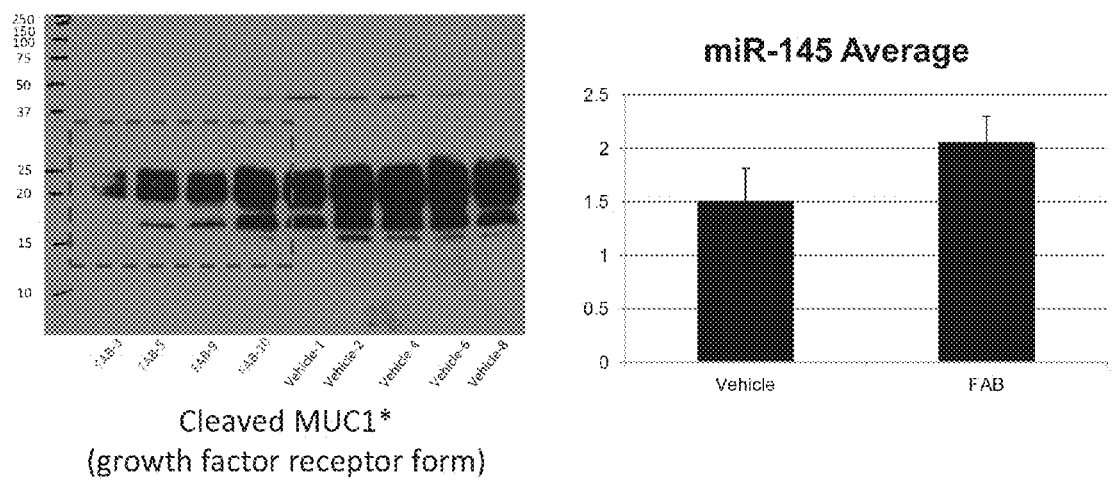
FIG. 20 shows Western blot and a graph of microRNA 145 levels from tumors excised from mice of the study, showing that in general, the tumors treated with the E6 Fab changed to have less MUC1* growth factor receptor than the control group and more microRNA145 which signals cells to differentiate.

In another in vivo study, male NOD/SCID mice were xenografted with human prostate tumors (DU-145). Tumors were allowed to develop for 14 days before treatment or mock treatment was begun. 60 days after tumor implantation the groups were switched; the mice receiving the cancer cell antibody E6 Fab were then given the buffer alone and the control group began receiving the E6 Fab. Treatment was with 160 mg/kg of the E6 Fab given every 24 hours. The graph of FIG. 19 shows that the treated group had significantly smaller tumors than the control group. Before the treatment groups were swapped, the tumors in the control group were more than 3-times larger than the treated group. In addition, only one of the treated mice had an increase in tumor growth when treatment was halted. FIG. 20 is a Western blot for MUC1* that shows that even after 2 weeks without treatment, the treated group on average had less MUC1* than the control group. Additionally, the graph of FIG. 20 shows that the treated group had an increase in the amount of microRNA-145 (miR-145) that they produced, which indicates that the E6 Fab treatment caused the cancer cells to differentiate which limited their ability to self-replicate.

Figure 21:
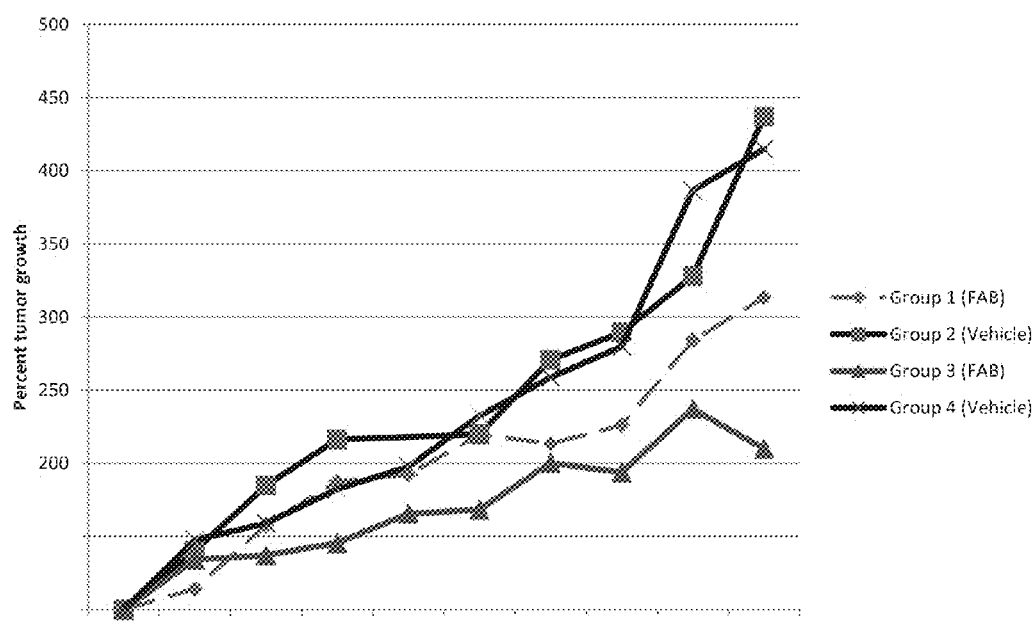
FIG. 21 shows a graph of tumor volume for NOD/SCID mice xenografted with human prostate tumor line DU145, wherein half the mice began treatment when their tumors averaged over 400 mm$^3$ and the other half began treatment when their tumors were between 175 mm$^3$ and 300 mm$^3$. Half of the large tumors were treated with the E6 Fab and the other half the vehicle alone. Similarly, the second group was divided into treated with E6 Fab at 160 mg/kg every 48 hours and the other half treated with vehicle alone. Results show that the Fab reduced tumor growth rate in both groups, however the group that began with the smaller tumors did much better.
Figure 26:
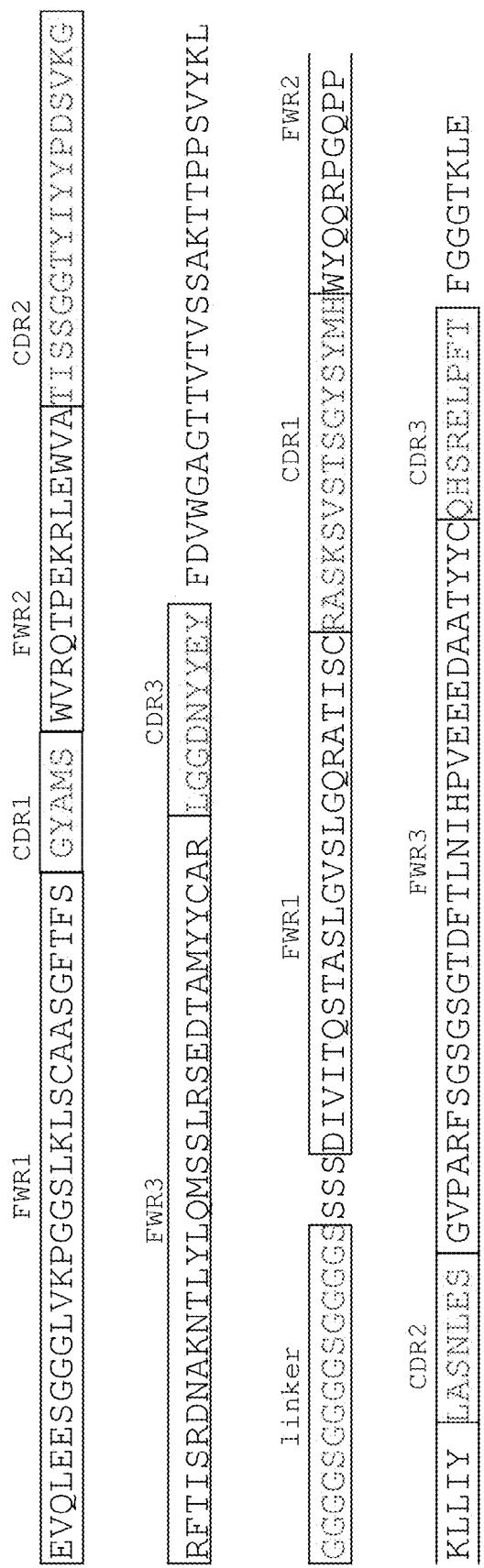
FIG. 26 shows the amino acid sequence of a MIN-C2 (single chain fragment variable) design (heavy chain variable-linker-light chain variable). The scFv construct was expressed in bacteria and purified using C-terminal poly-histidine (HHHHHH) tag.
Figure 27:
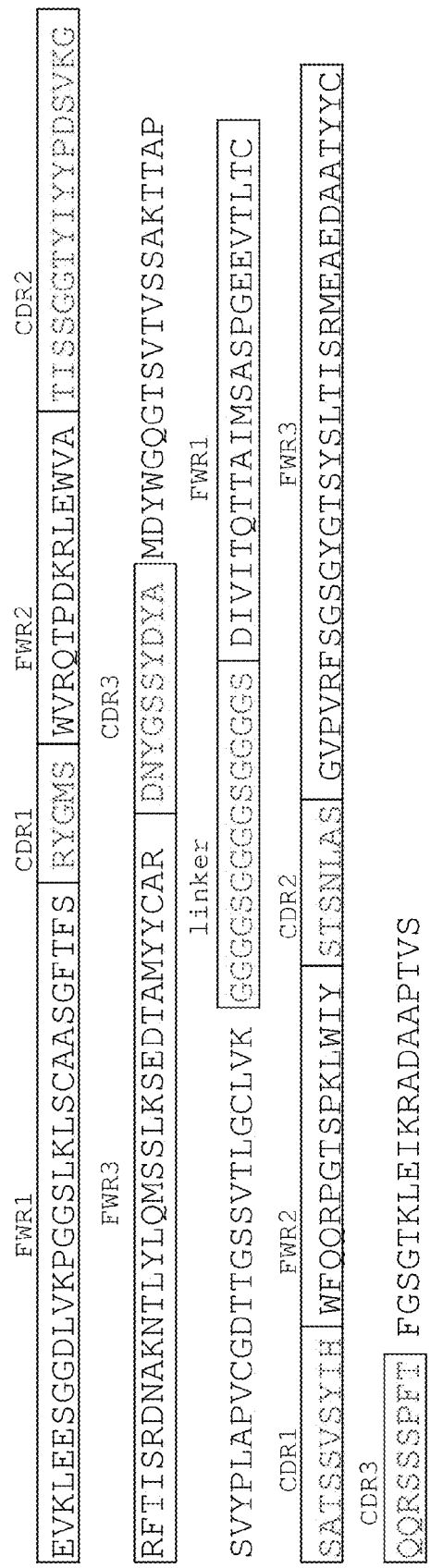
FIG. 27 shows the amino acid sequence of a MIN-E6 scFv (single chain fragment variable) design heavy chain variable (MIN-E6 VH7)-linker-light chain variable). The scFv construct was expressed in bacteria and purified using C-terminal poly-histidine (HHHHHH) tag.

In another animal study to test the efficacy of the cancer cell antibodies identified using methods of the invention, male NOD/SCID mice were xenografted with human prostate tumors (DU-145). Tumors were allowed to develop for 27 days before treatment or mock treatment was begun. The animals were divided into four groups wherein groups 1 and 2 had tumor volumes 350-500 mm$^3$ and groups 3 and 4 had tumor volumes 175-300 mm$^3$. Treatment was 160 mg/kg of the E6 Fab given every 24 hours (groups 1 and 3) and the mock treatment was buffer alone (groups 2 and 4). The graph of FIG. 21 shows that the tumors in the control mice grew at the same rate regardless of their starting volume. Although both treated groups had tumors that were much smaller than the control groups, mice whose tumors were in the 175-300 mm³ responded better than the groups bearing tumors 350-500 mm³ before treatment began. FIG. 22 shows representative photographs of the mice from the control group and FIG. 23 shows representative photographs of the mice from the treated group.

Thus, stem cell specific antibodies 2D6C3 and 2D6C8 (C3 and C8), as well as other monoclonal, polyclonals and antibody variants identified or selected using methods of the invention can be used much in the same way that ESAs and CSFs like Epogen and Leukine are used, including to accelerate the recovery of blood cells from effects of chemotherapy, used after bone marrow transplant, used before or after stem cell transplant which may be transplanted into the peripheral blood, and or to treat a patient who could benefit from increased production of hematopoietic stem cells or blood cells or their progenitors. There are several methods for humanizing stem cell specific antibodies 2D6C3 and 2D6C8 (C3 and C8), as well as other monoclonal, polyclonals and antibody variants identified or selected using methods of the invention, wherein constant regions of the mouse monoclonal antibodies are replaced with homologous human constant regions and wherein the variable region may be left as the mouse sequences or replaced by homologous human sequences. Phage display techniques can be used along with peptides of the invention to select the antibodies that bind best to the preferred MUC1* peptide. Alternatively, fully human antibody libraries can be screened de novo for their ability to bind to either the peptides used for selection of stem specific antibodies or the peptides used for selection of the cancer specific antibodies. If a stem specific antibody is desired, candidate antibodies can be screened for their ability to bind to cancer specific peptides in a de-selection process.

Cancer specific antibodies such as C2 (MIN-C2) and E6 (MIN-E6) as well as other monoclonal, polyclonals and antibody variants identified or selected using methods of the invention can be used to treat cancer patients with reduced risk of killing the patient's stem cells or blood cell precursors and progenitors. There are several methods for humanizing cancer specific antibodies C2 (MIN-C2) and E6 (MIN-E6), as well as other monoclonal, polyclonals and antibody variants identified or selected using methods of the invention, wherein constant regions of the mouse monoclonal antibodies are replaced with homologous human constant regions and wherein the variable region may be left as the mouse sequences or replaced by homologous human sequences. Phage display techniques can be used along with peptides of the invention to select the antibodies that bind best to the preferred MUC1* peptide. Alternatively, fully human antibody libraries can be screened de novo for their ability to bind to either the peptides used for selection of stem specific antibodies or the peptides used for selection of the cancer specific antibodies. If a cancer specific antibody is desired, candidate antibodies can be screened for their ability to bind to stem specific peptides in a de-selection process.

The invention includes antibodies as well as antibody-like proteins, including but not limited to polyclonal, monoclonal, chimeras, humanized, single chain, antibody fragments and the like. In addition, the invention includes the use of protein scaffolds for generating antibody mimics to obtain proteins that can be characterized by binding assays described herein and according to methods of the invention as being stem cell antibodies or cancer cell antibodies and thus being able to bind specifically to either MUC1* as it exists on cancer cells, or bind to MUC1* as it exists on stem cells, progenitor cells or engineered cells that express a form of MUC1*. The invention further includes using methods set forth here to identify antibodies that recognize specific epitopes, within the MUC1* extra cellular domain, that are expressed on different types of progenitor cells or non-tumor cancer cells.

In general, antibodies for the treatment of cancer should inhibit dimerization of MUC1* receptor. Thus in a preferred embodiment, antibodies for the treatment of MUC1-positive cancers are monovalent, such as Fabs, single chain antibodies, or bispecific antibodies. The invention does contemplate the use of antibodies such as pentavalent IgMs for the treatment of cancers because the multivalency acts to recluster the MUC1* extra cellular domain. However, bivalent antibodies at high enough concentration bind one antibody to each receptor rather than one antibody per each one receptor and in so doing are also inhibitory to cancer growth and development.

In general, antibodies of the invention that are suitable for stimulating stem and progenitor cell growth are bivalent such that they activate growth, survival and pluripotency pathways by dimerizing the MUC1* extra cellular domain. Stem and progenitor cell specific antibodies can be used to treat patient suffering from anemia, low white blood cell count, low platelets or any blood cell or blood progenitor cell deficiency. Additionally, the invention contemplates the use of stem and progenitor specific antibodies for use as anti-aging therapeutics, agents to promote overall health, agents to enhance stem or progenitor cell growth or to enhance engraftment of cells. Stem and progenitor specific antibodies described here may be administered to the patient systemically or locally, as an injection or as a topical treatment, as in a medicament for the eye or other areas of the body that are mechanically accessible.

Bivalent stem cell specific antibodies 2D6C3 and 2D6C8 (C3 and C8), as well as other monoclonal, polyclonals and antibody variants identified or selected using methods of the invention, can be used to stimulate stem cell growth in vitro or in vivo or can alternatively be used to enhance engraftment of stem cell transplants, irrespective of the source. In another embodiment, stem cell specific bivalent antibodies of the invention are used to stimulate the growth of hematopoietic stem cells in vitro or in vivo. In some cases stem cell antibodies are used to treat patients suffering from or at risk of developing anemia or low white blood count. These patients may be suffering from cancer and may be simultaneously treated with a cancer cell antibody of the invention for inhibiting their cancer cell growth.

In another aspect, antibodies and peptides of the invention are used for diagnosis. Contacting a patient's cells with a cancer specific antibody and getting significant binding would indicate that the patient has cancer. Similarly, contacting a patient's cells with a stem specific antibody and getting significant binding would indicate that the patient does not have cancer and would further identify those cells as stem or progenitor cells. A patient's cells can be contacted by both types of antibodies in order to distinguish stem cells from cancer cells. Such diagnosis can be carried out in vitro or in vivo. In vitro, a tissue specimen, blood sample, or bodily fluid sample can be analyzed using cancer or stem specific antibodies. In vivo, imaging agents can be attached to the antibodies of the invention to enable identification of cancer or stem cells in a patient.

EXAMPLES

Example 1—Development of Monoclonal Antibodies, 2D6C8 and 2D6C3 (Also Referred to Here as C3 and C8) that Facilitate Human Stem Cell Attachment to Surfaces MUC1* monoclonal antibodies were identified that preferentially bound to the portion of the MUC1* extra cellular domain that is more distal from the cell surface and these monoclonals were shown to better facilitate the attachment of human ES and iPS cells to surfaces. Mice were immunized with a peptide that is defined by the PSMGFR sequence. Supernatants of hybridoma clones were tested by ELISA for their ability to bind to the PSMGFR peptide and by FACS to determine which bound to live, MUC1* positive cells. Hybridomas were further selected if they preferentially bound to the PSMGFR peptide lacking 10 C-terminal amino acids, but did not bind if the peptide lacked the 10 N-terminal peptides. In addition, hybridomas were screened for their ability to facilitate stem cell attachment to a surface such as a plastic cell culture plate. Of these clones two, 2D6C8 and 2D6C3 were selected that when coated onto a surface captured stem cells and facilitated their growth.

What is claimed:

1. A method for treating a patient who would benefit from stimulation of the patient's stem cells, comprising administering to the patient an antibody that specifically binds to an epitope of the MUC1 protein expressed on human undifferentiated stem cells, wherein the antibody specifically binds to at least six consecutive amino acids of the peptide of SEQ ID NO:5, SEQ ID NO:6, SEQ ID NO:9, SEQ ID NO:10 or SEQ ID NO:11.

2. The method according to claim 1, wherein the patient suffers from cancer.

3. The method according to claim 2, wherein the patient suffers from cancer and is receiving chemotherapy or radiation.

4. The method according to claim 1, wherein the patient suffers from chronic kidney disease.

5. The method according to claim 1, wherein the antibody specifically binds to at least six consecutive amino acids of the peptide of SEQ ID NO:5.

6. The method according to claim 1, wherein the antibody specifically binds to at least six consecutive amino acids of the peptide of SEQ ID NO:6.

7. The method according to claim 1, wherein the antibody specifically binds to at least six consecutive amino acids of the peptide of SEQ ID NO:9.

8. The method according to claim 1, wherein the antibody specifically binds to at least six consecutive amino acids of the peptide of SEQ ID NO:10.

9. The method according to claim 1, wherein the antibody specifically binds to at least six consecutive amino acids of the peptide of SEQ ID NO:11.

10. The method of claim 1, wherein the antibody is humanized.

11. The method of claim 1, wherein the antibody is bi-valent.

12. A method for treating a patient who would benefit from stimulation of the patient's stem cells, comprising administering to the patient an antibody that specifically binds to an epitope of the MUC1 protein expressed on human undifferentiated stem cells, wherein the antibody does not bind or binds significantly less to at least six consecutive amino acids of the peptide of SEQ ID NO:3, SEQ ID NO:7 or SEQ ID NO:8.

13. The method according to claim 12, wherein the patient suffers from cancer.

14. The method according to claim 13, wherein the patient suffers from cancer and is receiving chemotherapy or radiation.

15. The method according to claim 12, wherein the patient suffers from chronic kidney disease.

16. The method of claim 12, wherein the antibody is humanized.

17. The method of claim 12, wherein the antibody is bi-valent.

18. A method for treating a patient diagnosed with a MUC1-positive cancer comprising administering to the patient a monovalent cancer cell-specific antibody and bivalent stem cell specific antibody, wherein the cancer cell-specific antibody specifically binds to at least six consecutive amino acids of the peptide of SEQ ID NO:3, SEQ ID NO:7 or SEQ ID NO:8 and does not bind to or binds significantly less to at least six consecutive amino acids of the peptide of SEQ ID NO:4, SEQ ID NO:5, SEQ ID NO:6, SEQ ID NO:9, SEQ ID NO:10 or SEQ ID NO:11.

19. The method according to claim 18, wherein the patient suffers from cancer and is receiving chemotherapy or radiation.

20. The method according to claim 18, wherein the patient suffers from chronic kidney disease.

21. The method of claim 18, wherein the antibody is humanized.

22. The method of claim 18, wherein the monovalent antibody is scFv or Fab.

23. A method for treating a patient diagnosed with a MUC1-positive cancer comprising administering to the patient a monovalent cancer cell-specific antibody and bivalent stem cell specific antibody, wherein the stem cell specific antibody specifically binds to at least six consecutive amino acids of the peptide of SEQ ID NO:4, SEQ ID NO:5, SEQ ID NO:6, SEQ ID NO:9, SEQ ID NO:10 or SEQ ID NO:11, and does not bind to or binds significantly less to at least six consecutive amino acids of the peptide of SEQ ID NO:3, SEQ ID NO:7 or SEQ ID NO:8.

24. The method of claim 23, wherein the antibody is humanized.

25. The method of claim 23, wherein the monovalent antibody is scFv or Fab.

26. A method for treating a patient suffering from cancer, comprising administering to a patient with MUC1-positive cancer cells an antibody that specifically binds to an epitope of the MUC1 protein that is expressed on cancer cells but is not expressed on human undifferentiated stem cells, comprising
obtaining an antibody that specifically binds to cancer cells, but not to stem cells comprising selecting antibodies that bind to at least six consecutive amino acids of a peptide of SEQ ID NO:3, SEQ ID NO:7 or SEQ ID NO:8, but do not bind or bind significantly less to at least six consecutive amino acids of the peptide of SEQ ID NO:4, SEQ ID NO:5, SEQ ID NO:6, SEQ ID NO:9, SEQ ID NO:10 or SEQ ID NO:11, wherein the antibody that specifically binds to cancer cells, but not to stem cells is obtained; and
administering the obtained antibody to the patient suffering from MUC-1 positive cancer.

27. The method according to claim 26, wherein the antibody is monovalent.

28. The method according to claim 27, wherein the antibody is scFv or Fab.

29. The method according to claim 26, wherein the antibody is humanized.

30. The method according to claim 26, wherein the patient suffers from cancer and is receiving chemotherapy or radiation.

31. The method according to claim 26, wherein the antibody specifically binds to at least six consecutive amino acids of the peptide of SEQ ID NO:3.

32. The method according to claim 26, wherein the antibody specifically binds to at least six consecutive amino acids of the peptide of SEQ ID NO:7.

33. The method according to claim 26, wherein the antibody specifically binds to at least six consecutive amino acids of the peptide of SEQ ID NO:8.

34. The method according to claim 31, wherein the antibody does not bind or binds significantly less to at least six consecutive amino acids of the peptide of SEQ ID NO:4.

35. A method of obtaining an antibody that specifically binds to stem cells, but not to cancer cells comprising the steps of:
(i) generating a mixed set of antibodies that recognize a peptide whose sequence is that of any of the peptides having the sequence of SEQ ID Nos: 1-11;
(ii) selecting those antibodies that bind to at least six consecutive amino acids of a peptide of SEQ ID NO:4, SEQ ID NO:5, SEQ ID NO:6, SEQ ID NO:9, SEQ ID NO:10 or SEQ ID NO:11, but do not bind or bind significantly less to at least six consecutive amino acids of the peptide of SEQ ID NO:3, SEQ ID NO:7 or SEQ ID NO:8;
(iii) selecting those antibodies that when adsorbed onto a solid surface facilitate the attachment of stem cells;
(iv) contacting the bivalent form of an antibody selected in both (i) and (ii) with stem cells, and with cancer cells;
(v) contacting the monovalent form of an antibody selected in both (i) and (ii) with stem cells, and with cancer cells; and
(vi) selecting and isolating an antibody that in the bivalent form stimulates the growth of stem cells and in the monovalent form inhibits the growth of stem cells, and wherein the bivalent and monovalent forms of the selected antibody have no significant effect on the growth of cancer cells.

36. The method according to claim 35, wherein the selected antibody binds to at least six consecutive amino acids of the peptide of SEQ ID NO:4, and does not bind or binds significantly less to at least six consecutive amino acids of the peptide of SEQ ID NO:3.

37. A method of obtaining an antibody that specifically binds to cancer cells, but not to stem cells comprising the steps of:

(i) generating a mixed set of antibodies that recognize a peptide whose sequence is that of any of the peptides having the sequence of SEQ ID Nos: 1-11;

(ii) selecting those antibodies that bind to at least six consecutive amino acids of a peptide of SEQ ID NO:3, SEQ ID NO:7 or SEQ ID NO:8, but do not bind or bind significantly less to at least six consecutive amino acids of the peptide of SEQ ID NO:4, SEQ ID NO:5, SEQ ID NO:6, SEQ ID NO:9, SEQ ID NO:10 or SEQ ID NO:11;

(iii) selecting those antibodies that when adsorbed onto a solid surface facilitate the attachment of cancer cells;

(iv) contacting the bivalent form of an antibody selected in both (i) and (ii) with stem cells, and with cancer cells;

(v) contacting the monovalent form of an antibody selected in both (i) and (ii) with stem cells, and with cancer cells; and (vi) selecting and isolating an antibody that in the bivalent form stimulates the growth of cancer cells and in the monovalent form inhibits the growth of cancer cells, and wherein the bivalent and monovalent forms of the selected antibody have no significant effect on the proliferation of stem cells.

38. The method according to claim 37, wherein the selected antibody binds to at least six consecutive amino acids of the peptide of SEQ ID NO:3, and does not bind or binds significantly less to at least six consecutive amino acids of the peptide of SEQ ID NO:4.

* * * * *